US011427626B2

(12) United States Patent
Bruno-Bonnet et al.

(10) Patent No.: US 11,427,626 B2
(45) Date of Patent: Aug. 30, 2022

(54) COMPOSITION OF FISH SKIN COLLAGEN PEPTIDES AND USE THEREOF AS A DRUG

(71) Applicant: GELATINES WEISHARDT, Graulhet (FR)

(72) Inventors: Christelle Bruno-Bonnet, Toulouse (FR); Yannick Auffret, Lisle sur Tarn (FR); Pascale Jolimaitre-Robert, Albi (FR); Patrice Corbille, Lasgraisses (FR)

(73) Assignee: GELATINES WEISHARDT, Graulhet (FR)

( * ) Notice: Subject to any disclaimer, the term of this patent is extended or adjusted under 35 U.S.C. 154(b) by 0 days.

(21) Appl. No.: 16/345,901

(22) PCT Filed: Oct. 24, 2017

(86) PCT No.: PCT/FR2017/052932
§ 371 (c)(1),
(2) Date: Apr. 29, 2019

(87) PCT Pub. No.: WO2018/078276
PCT Pub. Date: May 3, 2018

(65) Prior Publication Data
US 2019/0276515 A1 Sep. 12, 2019

(30) Foreign Application Priority Data

Oct. 28, 2016 (FR) ...................................... 1660521

(51) Int. Cl.
| C07K 14/78 | (2006.01) |
| A23L 33/18 | (2016.01) |
| A61P 1/14 | (2006.01) |
| A61P 29/00 | (2006.01) |
| A61P 31/10 | (2006.01) |
| A23J 3/34 | (2006.01) |
| B01D 15/34 | (2006.01) |
| B01D 15/36 | (2006.01) |
| C07K 14/46 | (2006.01) |
| A61K 35/60 | (2006.01) |
| A23L 33/17 | (2016.01) |
| A61K 38/01 | (2006.01) |
| C12P 21/06 | (2006.01) |
| A61K 38/00 | (2006.01) |

(52) U.S. Cl.
CPC .............. *C07K 14/78* (2013.01); *A23J 3/342* (2013.01); *A23L 33/17* (2016.08); *A23L 33/18* (2016.08); *A61K 35/60* (2013.01); *A61K 38/014* (2013.01); *A61P 1/14* (2018.01); *A61P 29/00* (2018.01); *A61P 31/10* (2018.01); *B01D 15/34* (2013.01); *B01D 15/363* (2013.01); *C07K 14/461* (2013.01); *C12P 21/06* (2013.01); *A23V 2002/00* (2013.01); *A61K 38/00* (2013.01)

(58) Field of Classification Search
None
See application file for complete search history.

(56) References Cited

U.S. PATENT DOCUMENTS

2009/0269455 A1* 10/2009 Hoffmann ............... A23J 3/342
                                                    426/564
2014/0296151 A1 10/2014 Gadre et al.

FOREIGN PATENT DOCUMENTS

| CN | 102428094 A | 4/2012 |
| FR | 2720067 A1 | 11/1995 |
| JP | 2007320946 A | 12/2007 |
| JP | WO2008059927 A1 | 3/2010 |
| WO | 2007090504 A1 | 8/2007 |
| WO | 2010074552 A1 | 7/2010 |
| WO | WO 2010/074552 * | 7/2010 |

OTHER PUBLICATIONS

Rodriguez-Diaz et al. (Journal of Food Science, vol. 76, Nr. 7, 2011) (Year: 2011).*
Baehaki, Journal of Chemical and Pharmaceutical Research, 2015, 7(11):131-135 (Year: 2015).*
"Identification of bioactive peptide from Oreochromis niloticus skin gelatin," Journal of Food Science and Technology, 2016, vol. 53, Issue 2, pp. 1222-1229.
International Search Report Interational Application No. PCT/FR2017/052932; International Filing Date: Oct. 24, 2017; dated Jan. 15, 2018; 4 pages.
International Search Report Interational Application No. PCT/FR2017/052932; International Filing Date: Oct. 24, 2017; dated Jan. 15, 2018; 5 pages.
Klotz et al., "Gelatin fragments block adherence of Candida albicans to extracellular matrix proteins" Microbiology, 1995, pp. 2681-2684.

(Continued)

*Primary Examiner* — Sergio Coffa
(74) *Attorney, Agent, or Firm* — Cantor Colburn LLP

(57) ABSTRACT

The invention relates to a composition of peptides having an aminogram in which: glycine, hydroxyproline and proline are in molar quantities such that the ratio of each quantity to the sum of the molar quantities of the amino acids in the composition is comprised between 20.0% and 24.5%, between 6.0% and 12.0% and between 10.6% and 14.6%, respectively; the peptide composition comprising a quantity of peptides with a molecular weight lower than 1400 Da such that the ratio of said quantity to the quantity of peptides in the composition is less than 40%; the molecular weight and the quantity of peptides in the composition being determined by exclusion chromatography. The invention likewise relates to such a composition to be used as a drug. The invention further relates to such a composition to be used as a food supplement.

14 Claims, 10 Drawing Sheets

(56) References Cited

OTHER PUBLICATIONS

Liang et al., "The Protective Effects of Long-Term Oral Administration of Marine Collagen Hydrolysate from Chum Salmon on Collagen Matrix Homeostasis in the Chronological Aged Skin of Sprague-Dawley Male Rats," Journal of Food and Science, 2010, vol. 75, Issue 8, pp. 2-5.
Ramadass et al., "Type I collagen ad its daughter peptides for targeting mucosal healing in ulcerative colitis: A new treatment strategy," European Journal of Pharmaceutical Sciences, vol. 91, pp. 216-224.
Written Opinion Interational Application No. PCT/FR2017/052932; International Filing Date: Oct. 24, 2017 dated Jan. 15, 2018; 7 pages.
Zhang et al., "Purifications and characterization of novel antioxidant peptides from enzymatic hydrolysates of tilapia (*Oreochromis niloticus*) skin gelatin," Peptides, 2012, vol. 38, Issue 1, pp. 13-21.
China Office Action dated May 31, 2022, Application No. 201780066941.7 (11 pages) (English on pp. 8-9).
Fan et al., "Studis on Physical and Chemical Properties of Collagen Peptides from Walleye Pollock Skin", Acta Academiae Medicinae Qingdao Universitatis, vol. 49, No. 6, Dec. 2013, 3 pages (English abstract).

\* cited by examiner

COMPOSITION OF FISH SKIN COLLAGEN PEPTIDES AND USE THEREOF AS A DRUG

CROSS REFERENCE TO RELATED APPLICATIONS

This application is a National Stage application of PCT/FR2017/052932, filed Oct. 24, 2017, which claims the benefit of France Application No. 16.60521, filed Oct. 28, 2016, both of which are incorporated by reference in their entirety herein.

The invention relates to a composition of collagen peptides from fish skin(s). The invention relates in particular to such a peptide composition obtained by enzymatic hydrolysis of collagen from fish skin(s). The invention also relates to such a composition for use thereof as medicament. The invention therefore relates to the use of such a composition for the curative or preventative treatment of a disease affecting the human or animal body. The invention in particular relates to such a composition for use thereof as medicament in the treatment of a digestive candidiasis in humans or animals and/or in the treatment of an intestinal inflammation in humans or animals. The invention also relates to such a composition for use thereof as medicament in a microbiota-stimulating treatment.

FR 2 720 067 discloses a peptide powder obtained by hydrolysis by papain of a collagen-rich starting material originating from the skin or the skeleton of fish, mollusks or crustaceans. In the peptide powder obtained, 38% of the peptides have a molecular weight of between 10 000 Da and 50 000 Da. The peptide composition of FR 2 720 067 has a broad range of molecular weights, in particular a proportion of greater than 10% of peptides with a molecular weight of greater than 10 000 Da. The peptide composition of FR 2 720 067 is heterogeneous by the size of the peptides and has a fraction of water-soluble peptides of only between 80% and 90%. Such powders of peptides of high molecular weight greater than 10 000 Da are not perfectly water-soluble. They are also not entirely absorbable by the digestive tract and therefore pose problems in terms of their bioavailability.

FR 2 720 067 also describes the use of such a peptide powder obtained from fish living at great depth in the curative treatment of inflammation of the tendons of joints of the lower limbs (knees, fetlocks and hooves) of racehorses. Obtaining such a composition is problematic. This is because it requires the removal of deep-sea fish. In addition, such a powder is limited in its use to the treatment of joint inflammation.

The invention therefore aims to overcome these drawbacks.

The invention aims to propose a novel peptide composition resulting from an enzymatic hydrolysis of collagen from skin(s) of temperate-water fish, said peptides being water-soluble—that is to say 100% water-soluble—and entirely absorbable by the digestive tract.

The invention also aims to propose a novel peptide composition formed by enzymatic hydrolysis of collagen from skin(s) of temperate-water fish.

The invention also aims to propose such a peptide composition that is capable of being used as medicament.

The invention in particular aims to propose such a peptide composition resulting from an enzymatic hydrolysis of collagen from skin(s) of temperate-water fish that is capable of being used as medicament.

The invention aims to propose such a peptide composition having both a distribution of the apparent molecular weights of said peptides that extends over a narrow range of between approximately one hundred and a few thousands of Daltons, that is to say excluding peptides of high apparent molecular weight, and also having a low proportion of peptides of low apparent molecular weight.

The invention aims to propose such a peptide composition that is capable of being used as medicament in the treatment of intestinal candidiasis.

The invention also aims to propose such a peptide composition that is capable of being used as medicament in the treatment of inflammatory digestive diseases, especially inflammatory bowel diseases (IBDs).

The invention also aims to propose such a peptide composition that is capable of being used to promote equilibrium and maintenance of the intestinal flora (or microbiota).

The invention also aims to propose the use of such a peptide composition resulting from an enzymatic hydrolysis of collagen from skin(s) of temperate-water fish as dietary supplement.

For this purpose, the invention relates to a peptide composition having an aminogram in which:
  glycine is in a molar amount such that the ratio of this amount to the sum of the molar amounts of the amino acids in the composition is between 20.0% and 24.5%;
  hydroxyproline is in a molar amount such that the ratio of this amount to the sum of the molar amounts of the amino acids in the composition is between 6.0% and 12.0%, especially between 7.0% and 11.0%;
  proline is in a molar amount such that the ratio of this amount to the sum of the molar amounts of the amino acids in the composition is between 10.6% and 14.6%, especially between 11.6% and 13.6%, in particular between 12.1% and 13.1%, preferably of the order of 12.6%; the peptide composition having, during analysis by exclusion chromatography during which each peptide of the peptide composition is eluted with a retention time that is representative of the apparent molecular weight of this peptide, an elution curve (that is to say an elution curve of a chromatogram) of the peptides having an area under the curve value (that is to say an area value representative of the amount by weight of peptides) corresponding to the peptides of apparent molecular weight of less than 1400 Da such that the ratio of this area value to the total area under the curve (corresponding to all the peptides of the composition) is less than 40%, especially less than 38%, preferably between 30% and 38%, in particular between 30% and 35%;
said analysis being performed as described below:
  on a filtration column of dimensions 300×7.8 mm comprising a stationary phase formed of a silica gel with a porosity of 5 µm;
  the column being kept at a temperature of 40° C.;
  with, as mobile phase, a solution formed (A) of ultrapure water comprising 0.1% by volume of trifluoroacetic acid and (B) of acetonitrile, wherein the A/B volume ratio is 75/25;
  introducing, at the top of the gel filtration column, a volume of a solution comprising the peptide composition;
  the flow rate of the mobile phase in the column being 0.6 ml/min, and;
  the peptides of the composition being detected by absorbance at a wavelength of 214 nm.

Throughout the text, "aminogram" in intended to mean the list of the free amino acids forming, by peptide chain (or bonding), the sequence of a peptide or the sequence of peptides of a mixture of peptides. Such an aminogram is obtained by analysis—especially by overall analysis or sequence analysis—of the amino acids constituting a peptide or a mixture of peptides.

In particular, the nature and the amount of the amino acids constituting the peptides of the composition according to the invention are determined by any method of overall analysis known per se to those skilled in the art. In particular, this analysis is carried out in accordance with standard ISO 13903:2005 by assay of the free and total amino acids using an amino acid analyzer or using high performance liquid chromatography (HPLC) equipment. Hydroxyproline is assayed by continuous flow analysis and colorimetric detection.

The aminogram obtained by overall analysis of the composition according to the invention is representative of the amino acid composition of collagen from skins of temperate-water fish. The invention therefore relates to such a peptide composition resulting from the enzymatic hydrolysis of collagen from skins of temperate-water fish by a cysteine protease of plant origin—especially a protease from the class EC 3.4.22.2-. The inventors have discovered that the use of such a cysteine protease makes it possible to obtain a composition of peptides which are water-soluble—that is to say 100% water-soluble—and which are entirely absorbable by the digestive tract and which have a distribution of apparent molecular weights which extends over a narrow range between approximately one hundred and a few thousands of Daltons, that is to say excluding peptides of high apparent molecular weights, and also having a low proportion of peptides of low apparent molecular weights.

In addition, a separation of the peptides of the peptide composition according to the invention is carried out as a function of their apparent molecular weight, by subjecting the peptide composition to a step of analytical separation by liquid chromatography on a porous silica gel filtration column (BioSep-SEC-S2000, Phenomenex, Le Peck, France) with a high surface density of silanol groups.

Use is made, as mobile phase, of a solution comprising (A) ultrapure water with trifluoroacetic acid (0.1% by volume) added thereto and (B) acetonitrile (A/B; 75/25; v/v). The gel filtration column is kept at a temperature of 40° C. during the analysis. The flow rate of the mobile phase in the stationary phase is 0.6 ml/min. The volume of peptide composition to be analyzed, introduced at the top of the gel filtration column, is 25 µl and the detection is carried out continuously by absorbance at a wavelength of 214 nm. A chromatogram is obtained, on which each peak is characterized by a duration or retention time value (expressed in minutes following the introduction of the mixture to be analyzed at the top of the column) determined at the maximum absorbance value of the peak. The apparent molecular weight of each peptide corresponding to this retention time value at the maximum absorbance value of each peak is determined by means of a predetermined calibration curve obtained by analysis—under the same chromatographic conditions as described above—of peptides of determined apparent molecular weights. For example, such a calibration curve is produced by analyzing, under these same chromatographic conditions, a mixture of reference peptides/proteins with known apparent molecular weights of between 100 Da and 30 kDa.

With the chromatogram representing the variation in absorbance at 214 nm over the course of the chromatographic analysis of the peptide composition of the invention, the proportion of peptides of apparent molecular weight of less than 1400 Da is determined by evaluating the ratio of the value of the area under the curve—that is to say the value of the sum of the areas under the peaks of the curve—corresponding to the peptides of apparent molecular weight of less than 1400 Da to the value of the total area under the whole of the curve—that is to say the value of the sum of the areas under each peak of the curve—and corresponding to all the peptides of the peptide composition.

The invention therefore relates to a composition of peptides resulting from an enzymatic hydrolysis of collagen from skins of temperate-water fish by a cysteine protease of plant origin, each peptide of the composition having a number of amino acids of between 2 and a few tens, preferably of between 2 amino acids and 100 amino acids.

In some embodiments, the composition according to the invention has an aminogram in which glycine is in a molar amount such that the ratio of this amount to the sum of the molar amounts of the amino acids in the composition is between 20.0% and 22.4%, especially between 20.0% and 21.9%, in particular between 20.4% and 21.4%.

In some other embodiments, the composition according to the invention has an aminogram in which glycine is in a molar amount such that the ratio of this amount to the sum of the molar amounts of the amino acids in the composition is between 22.4% and 24.9%, especially between 22.9% and 24.4%, in particular between 23.0% and 24.0%.

In some embodiments, the composition according to the invention has an aminogram in which hydroxyproline is in a molar amount such that the ratio of this amount to the sum of the molar amounts of the amino acids in the composition is between 7.0% and 9.0%, in particular between 7.5% and 8.5%, preferably between 7.7% and 8.5%.

In some other embodiments, the composition according to the invention has an aminogram in which hydroxyproline is in a molar amount such that the ratio of this amount to the sum of the molar amounts of the amino acids in the composition is between 9.5% and 11.5%, in particular between 10.0% and 11.0%, preferably of the order of 10.5%.

In some embodiments, the composition according to the invention has an aminogram in which glutamic acid is in a molar amount such that the ratio of this amount to the sum of the molar amounts of the amino acids in the composition is between 8.0% and 13.0%.

In some embodiments, the composition according to the invention has an aminogram in which glutamic acid is in a molar amount such that the ratio of this amount to the sum of the molar amounts of the amino acids in the composition is between 8.0% and 10.0%, in particular between 8.5% and 9.5%, preferably between 9.0% and 9.5%.

In some other embodiments, the composition according to the invention has an aminogram in which glutamic acid is in a molar amount such that the ratio of this amount to the sum of the molar amounts of the amino acids in the composition is between 10.5% and 12.5%, in particular between 11.0% and 12.0%, preferably of the order of 11.6%.

In some embodiments, the composition according to the invention has an aminogram in which arginine is in a molar amount such that the ratio of this amount to the sum of the molar amounts of the amino acids in the composition is between 6.9% and 10.9%, especially between 7.9% and 9.9%, in particular between 8.0% and 9.0%.

In some embodiments, the composition according to the invention has an aminogram in which alanine is in a molar amount such that the ratio of this amount to the sum of the molar amounts of the amino acids in the composition is between 7.3% and 11.5%, especially between 8.0% and 10.0%, in particular between 8.1% and 9.6%.

In some embodiments, the composition according to the invention has an aminogram in which aspartic acid is in a molar amount such that the ratio of this amount to the sum of the molar amounts of the amino acids in the composition is between 3.1% and 7.1%, especially between 4.1% and 6.1%, in particular between 4.6% and 5.6%, preferably between 5.0% and 5.5%.

In some embodiments, the composition according to the invention has an aminogram in which lysine is in a molar amount such that the ratio of this amount to the sum of the molar amounts of the amino acids in the composition is between 1.5% and 5.5%, especially between 2.5% and 4.5%, in particular between 3.0% and 4.0%, preferably between 3.1% and 3.6%.

In some embodiments, the composition according to the invention has an aminogram in which serine is in a molar amount such that the ratio of this amount to the sum of the molar amounts of the amino acids in the composition is between 1.5% and 5.5%, especially between 2.5% and 4.5%, in particular between 3.0% and 4.0%, preferably between 3.2% and 3.6%.

In some embodiments, the composition according to the invention has an aminogram in which threonine is in a molar amount such that the ratio of this amount to the sum of the molar amounts of the amino acids in the composition is between 0.7% and 4.7%, especially between 1.7% and 3.7%, in particular between 2.2% and 3.2%, preferably between 2.4% and 2.8%.

In some embodiments, the composition according to the invention has an aminogram in which leucine is in a molar amount such that the ratio of this amount to the sum of the molar amounts of the amino acids in the composition is between 0.6% and 4.6%, especially between 1.6% and 3.6%, in particular between 2.1% and 3.1%, preferably between 2.4% and 2.9%.

In some embodiments, the composition according to the invention has an aminogram in which phenylalanine is in a molar amount such that the ratio of this amount to the sum of the molar amounts of the amino acids in the composition is between 0.3% and 4.3%, especially between 1.3% and 3.3%, in particular between 1.8% and 2.8%, preferably between 1.8% and 2.4%.

In some embodiments, the composition according to the invention has an aminogram in which valine is in a molar amount such that the ratio of this amount to the sum of the molar amounts of the amino acids in the composition is between 0 and 4.0%, especially between 1.0% and 3.0%, in particular between 1.5% and 2.5%, preferably between 1.8% and 2.5%.

In some embodiments, the composition according to the invention has an aminogram in which isoleucine is in a molar amount such that the ratio of this amount to the sum of the molar amounts of the amino acids in the composition is between 0 and 3.5%, especially between 0.5% and 2.5%, in particular between 0.9% and 2.0%, preferably between 0.9% and 1.6%.

In some embodiments, the composition according to the invention has an aminogram in which hydroxylysine is in a molar amount such that the ratio of this amount to the sum of the molar amounts of the amino acids in the composition is between 0 and 3.5%, especially between 0.5% and 2.5%, in particular between 1.0% and 2.0%, preferably of the order of 1.5%.

In some embodiments, the composition according to the invention has an aminogram in which histidine is in a molar amount such that the ratio of this amount to the sum of the molar amounts of the amino acids in the composition is between 0 and 3.3%, especially between 0 and 2.3%, in particular between 0.5% and 1.5%.

In some embodiments, the composition according to the invention has an aminogram in which methionine is in a molar amount such that the ratio of this amount to the sum of the molar amounts of the amino acids in the composition is between 0 and 2.5%, especially between 0 and 2.0%, in particular between 0.5% and 1.8%, preferably between 0.7% and 1.6%.

In some embodiments, the composition according to the invention has an aminogram in which tyrosine is in a molar amount such that the ratio of this amount to the sum of the molar amounts of the amino acids in the composition is between 0 and 1.5%, especially between 0 and 1.0%, in particular between 0 and 0.9%, preferably between 0.2% and 0.8%.

In some embodiments, the composition according to the invention has an aminogram in which cysteine and cystine are in a molar amount such that the ratio of this amount to the sum of the molar amounts of the amino acids in the composition is between 0 and 2%, especially between 0 and 1.0%, in particular between 0 and 0.5%, preferably of the order of 0.03%.

The composition according to the invention has an aminogram in which the essential amino acids (lysine, methionine, phenylalanine, threonine, valine, leucine and isoleucine and histidine) are together between 15% and 20%.

Advantageously, in some embodiments according to the invention, at least 90%—especially at least 95%—of the peptides of the peptide composition have an apparent molecular weight of less than 15 000 Da (Daltons), especially of between 200 Da and 15 000 Da, preferably of between 200 Da and 14 000 Da, in particular of between 200 Da and 13 000 Da. Advantageously, in some embodiments according to the invention, at least 90% of the peptides of the composition have an apparent molecular weight of between 200 Da and 12 000 Da.

The peptides of the composition according to the invention have a tight distribution of apparent molecular weights, extending over a narrow range of between approximately one hundred and a few thousands of Daltons, that is to say excluding peptides of high apparent molecular weights having more than 100 amino acids, and also having a low proportion of peptides of low apparent molecular weights.

Advantageously, in some embodiments according to the invention, the peptides of the composition have a mean apparent molecular weight value of between 2500 Da and 3600 Da, especially of between 2700 Da and 3600 Da. Since each peptide of the peptide composition according to the invention makes a weight contribution to the composition, the mean apparent molecular weight value of peptides of the composition corresponds to the mean of each value, referred to as the weighted value, of the apparent molecular weight of each weighted peptide by a value representative of the weight contribution of each peptide in the composition. The value representative of the weight contribution of each peptide or group of peptides in the composition is expressed as a percentage of the value of the area under the curve corresponding to said peptide or to said group of peptides over the value of the total area under the curve corresponding to all the peptides of the composition.

In practice, the weighted apparent molecular weight value of a group of peptides corresponding to the same peak of a chromatogram corresponds to the apparent molecular weight value read off at the top (maximum) of this peak of the chromatogram, multiplied by the ratio of the value of the area under the curve of this peak to the (total) area under the curve of the chromatogram. "Area under the curve" or "area under the peak" is intended to mean the area of the space between the curve tracing the peak of the chromatogram and the baseline of the chromatogram. In particular, the area under one of the peaks of the chromatogram extends between two minima of the curve of the chromatogram, enclosing a top (or maximum) of the curve of the chromatogram.

According to some embodiments, the peptide composition according to the invention has, during analysis thereof by exclusion chromatography during which each peptide of the peptide composition is eluted with a retention time that is representative of the apparent molecular weight of this peptide, a curve representative of the elution (that is to say a chromatogram) of the peptides having a value of the area under this curve (that is to say an area value representative of the amount by weight of peptides) corresponding to the peptides of apparent molecular weight of greater than 10 000 Da—especially of between 10 000 Da and 50 000 Da such that the ratio of this area value to the total area under the curve (corresponding to all the peptides of the composition) is less than 15%, especially less than 10%. According to some particular embodiments, this ratio is between 2.5% and 8.5%.

According to other particular embodiments, the peptide composition according to the invention may be devoid of any peptide of high molecular weight. According to these other particular embodiments, the peptide composition according to the invention is formed of water-soluble peptides.

According to some embodiments, the peptide composition according to the invention has, during analysis thereof by exclusion chromatography during which each peptide of the peptide composition is eluted with a retention time that is representative of the apparent molecular weight of this peptide, a curve representative of the elution (that is to say a chromatogram) of the peptides having a value of the area under this curve (that is to say an area value representative of the amount by weight of peptides) corresponding to the peptides of apparent molecular weight of between 1800 Da and 10 000 Da such that the ratio of this area value to the total area under the curve (corresponding to all the peptides of the composition) is greater than 35%—especially between 35% and 70%, in particular between 45% and 65%. According to some particular embodiments, this ratio is between 49% and 55%.

According to some embodiments, the peptide composition according to the invention has, during analysis thereof by exclusion chromatography during which each peptide of the peptide composition is eluted with a retention time that is representative of the apparent molecular weight of this peptide, a curve representative of the elution (that is to say a chromatogram) of the peptides having a value of the area under this curve (that is to say an area value representative of the amount by weight of peptides) corresponding to the peptides of apparent molecular weight of between 600 Da and 1800 Da such that the ratio of this area value to the total area under the curve (corresponding to all the peptides of the composition) is between 15% and 45%—especially between 20% and 40%, in particular between 25% and 35%. According to some particular embodiments, this ratio is between 27% and 32%.

According to some embodiments, the peptide composition according to the invention has, during analysis thereof by exclusion chromatography during which each peptide of the peptide composition is eluted with a retention time that is representative of the apparent molecular weight of this peptide, a curve representative of the elution (that is to say a chromatogram) of the peptides having a value of the area under this curve (that is to say an area value representative of the amount by weight of peptides) corresponding to the peptides of apparent molecular weight of less than 600 Da such that the ratio of this area value to the total area under the curve (corresponding to all the peptides of the composition) is less than 10%. According to some particular embodiments, this ratio is between 8.5% and 14.5%.

Advantageously, the composition according to the invention has, by chromatographic analysis on an anion exchange column during which each peptide of the peptide composition is eluted from the column with a retention time that is representative of its charge:
  an area value under a peak corresponding to the anionic peptides;
  an area value under a peak corresponding to the neutral peptides, and;
  an area value under a peak corresponding to the cationic peptides;
such that the ratio of this area value under the peak corresponding to the anionic peptides to the sum of the area values under the peaks corresponding to the anionic peptides, to the neutral peptides and to the cationic peptides of the composition is between 27.0% and 45%, especially between 30% and 45%, in particular between 35% and 43%, preferably between 35% and 40%;
the value of the area under the peak corresponding to the anionic peptides, the value of the area under the peak corresponding to the cationic peptides and the value of the area under the peak corresponding to the neutral peptides being determined by chromatographic analysis under the conditions described below:
  using a chromatographic column of dimensions 100×7.8 mm comprising, as stationary phase, a hydrophilic anion exchange resin functionalized with quaternary ammonium groups with a particle size of 10 μm;
  using, as first mobile phase for elution of the cationic peptides and neutral peptides, a 5 mM aqueous Tris buffer (C) at pH 8.35 for a duration of 7 minutes starting from the introduction of the composition to be analyzed at the top of the column, then a second mobile phase for elution of the anionic peptides, in which the ratio of the volume of a buffer (D) formed of 5 mM Tris, 5 M NaCl at pH 8.35 to the volume of buffer (C) increases linearly from 0 to 100% in 30 minutes;
  with a flow rate of the mobile phase of 1 ml/min in the column;
  the analysis being performed at a temperature of 25° C., and;
  with detection by absorbance at a wavelength of 214 nm at the column outlet.

Advantageously according to the invention, the peptides of the composition according to the invention have, during a reversed-phase liquid chromatography hydrophobicity analysis, a retention time of between 16 min and 36 min; said hydrophobicity analysis being performed under the conditions below:
  using a chromatography column of dimensions 250×4.6 mm having a stationary phase formed of silica grafted with butyl groups, of a particle size of 5 μm and of a porosity value of 300 Å;
  using, as first mobile phase for elution of the hydrophilic peptides, a solution (E) of trifluoroacetic acid at 0.1% in ultrapure water for a duration of 7 minutes starting from the introduction of the composition to be analyzed at the top of the column, then a second mobile phase for elution of the hydrophobic peptides in which the ratio of the volume of a solution (F) of trifluoroacetic acid at 0.1% (by volume) in water comprising 40% acetonitrile to the volume of the solution (E) increases linearly from 0 to 40% in 30 minutes;

with a flow rate of the mobile phase of 0.6 ml/min in the column;

the analysis being performed at a temperature of 40° C., and;

with detection by absorbance at a wavelength of 214 nm at the column outlet.

In some embodiments, a composition according to the invention comprises peptides which are hydrophobic by nature which are eluted from the column mentioned above and under the conditions specified above with a retention time corresponding to a percentage of acetonitrile of between 12% and 38%. The median retention time of the peptides of the composition according to the invention is 26 min, corresponding to a percentage of acetonitrile of 25% in the eluent.

Advantageously according to the invention, the peptide composition is in the liquid state. It may be a solution of the peptide composition according to the invention in a liquid solvent, especially in an aqueous solvent.

Advantageously according to the invention, the peptide composition is in the solid state. The peptide composition may be in the form of a solid in the divided state. It may in particular be a solid in the at least partially dehydrated state. The peptide composition according to the invention may be in powder form.

Advantageously according to the invention, the peptide composition is devoid of carbohydrates.

Advantageously according to the invention, the peptide composition is devoid of fats.

Advantageously according to the invention, the solids of the peptide composition comprises a proportion by weight of collagen peptides of greater than 95%, especially greater than 99%. Thus, the peptide composition has an amount of collagen peptides such that the weight ratio of the collagen peptides of the solids of the peptide composition to the solids of the peptide composition is greater than 95%, especially greater than 99%.

Advantageously according to the invention, the peptides of the composition are water-soluble. Advantageously, the peptides of the peptide composition are 100% water-soluble. Advantageously, the peptide composition is hydrocompatible.

Advantageously according to the invention, the peptides of the peptide composition result from a controlled enzymatic hydrolysis of collagen from skin of at least one fish selected from the group formed of fish from the family Pangasiidae—especially *Pangasius hypophtalmus* (or *Pangasianodon hypophtalmus*), *Pangasius pangasius, Pangasius bocourti*—and from the family Cichlidae—especially from the genus *Oreochromis*, in particular *Oreochromis niloticus* or from the genus *Tilapia*. Advantageously, the peptides of the peptide composition result from a controlled enzymatic hydrolysis of collagen from skin of at least one fish found in a temperate water of a temperate region.

The invention also extends to the use of such a peptide composition in a therapeutic treatment for the human or animal body. The invention therefore also extends to such a peptide composition for use thereof as medicament. The invention therefore extends to such a peptide composition for use thereof as medicament in the preventative or curative treatment of at least one disease of the human or animal body.

The invention also extends in particular to a peptide composition for use thereof as medicament in at least one of the following treatments:
treatment of a digestive disease;
treatment of an intestinal candidiasis;
treatment of a digestive inflammation, and;
maintenance of the intestinal microbiota.

The invention also extends to any use of the peptide composition according to the invention in human food. According to some embodiments, the invention also extends to any use of a peptide composition according to the invention in human food, excluding any use as medicament. In particular, the composition according to the invention is advantageously used as dietary supplement.

The invention also extends to a peptide composition obtained by a process in which:
skins of temperate-water fish are selected—especially from the family of the Pangasiidae and/or from the family of the Cichlidae, then;
the following are carried out in succession:
at least one step of washing the skins, then;
at least one step of acid or alkaline treatment of the skins, suitable for enabling extraction of at least a portion of the collagen from the skins, then;
at least one step of hydrolysis of the collagen by at least one cysteine protease of plant origin—in particular at least one protease of *Carica papaïa*—at a temperature of less than 75° C., then;
interruption of the enzymatic hydrolysis by heating the collagen hydrolyzate to a temperature greater than the denaturation temperature of each cysteine protease, so as to form the peptide composition.

Advantageously, in a process according to the invention, after the step of acid or alkaline treatment of the skins, at least one liquid/solid extraction of the collagen is carried out in water brought to a temperature of between 60° C. and 98° C. Advantageously, in a process according to the invention, a step of separation is next carried out—especially a step of separation by settling out—of a fraction comprising solids (and fats) and of a solution comprising the extracted collagen, then the solution comprising the extracted collagen is subjected to a purification step, for example by filtration over earth and/or demineralization on an ion exchange resin, suitable for forming a purified solution comprising collagen, the solids of the purified solution comprising a proportion by weight of collagen of at least 99%, especially at least 99.5%, in particular at least 99.8%. A purified solution of collagen is formed, comprising substantially pure collagen. In particular, such a purified solution of collagen is formed which is substantially colorless. In particular, such a purified solution of collagen is formed which is substantially—especially totally—devoid of elastin. The purified solution is concentrated so as to form a purified collagen gel, and the purified collagen gel is then subjected to the step of hydrolysis of the collagen.

Such a process makes it possible to obtain a peptide composition according to the invention which is substantially colorless. Such a process makes it possible to obtain a peptide composition according to the invention which is substantially devoid of elastin. In particular, it makes it possible to obtain such a peptide composition according to the invention without any chromatographic step of purification of the peptide composition.

In such a process, advantageously and according to the invention, a subsequent step of filtration of the peptide composition is carried out. Advantageously, a step of pasteurization of the peptide composition is also carried out for a duration of at least 2 minutes at a pasteurization temperature of between 85° C. and 90° C. at least.

In such a process, advantageously and according to the invention, a step of drying the peptide composition is carried out. This drying step is carried out by spray drying so as to form a composition according to the invention that is substantially dehydrated and in powder form.

The invention therefore extends to a peptide composition obtained by a process in which:
skins of temperate-water fish are selected—especially from the family of the Pangasiidae and/or from the family of the Cichlidae, then;
the following are carried out in succession:
at least one step of washing the skins, then;
at least one step of acid treatment of the skins, suitable for enabling extraction of at least a portion of the collagen from the skins, then;
at least one step of hydrolysis of the collagen by at least one cysteine protease of plant origin—in particular at least one protease of *Carica papaïa*—at a temperature of less than 75° C., then;
interruption of the enzymatic hydrolysis by heating the collagen hydrolyzate to a temperature greater than the denaturation temperature of each cysteine protease, so as to form the peptide composition;
said peptide composition having an overall analysis of the amino acids in which:
glycine is in a molar amount such that the ratio of this amount to the sum of the molar amounts of the amino acids in the composition is between 20.0% and 24.5%;
hydroxyproline is in a molar amount such that the ratio of this amount to the sum of the molar amounts of the amino acids in the composition is between 6.0% and 12.0%;
proline is in a molar amount such that the ratio of this amount to the sum of the molar amounts of the amino acids in the composition is between 10.6% and 14.6%;
the peptide composition having, during analysis by exclusion chromatography during which each peptide of the peptide composition is eluted with a retention time that is representative of the apparent molecular weight of this peptide, an elution curve (that is to say an elution curve of a chromatogram) of the peptides having an area under the curve value (that is to say an area value representative of the amount by weight of peptides) corresponding to the peptides of apparent molecular weight of less than 1400 Da such that the ratio of this area value to the total area under the curve (corresponding to all the peptides of the composition) is less than 40%;
said analysis being performed as described below:
on a filtration column of dimensions 300×7.8 mm comprising a stationary phase formed of a silica gel with a porosity of 5 µm;
the column being kept at a temperature of 40° C.;
with, as mobile phase, a solution formed (A) of ultrapure water comprising 0.1% by volume of trifluoroacetic acid and (B) of acetonitrile, wherein the A/B volume ratio is 75/25;
introducing, at the top of the gel filtration column, a volume of a solution comprising the peptide composition;
the flow rate of the mobile phase in the column being 0.6 ml/min, and;
the peptides of the composition being detected by absorbance at a wavelength of 214 nm.

The invention also relates to a peptide composition, such a peptide composition for use thereof as medicament, a process for obtaining such a peptide composition and such a peptide composition obtained by such a process for obtaining same, characterized in combination by all or a portion of the characteristics mentioned above or below.

Other aims, characteristics and advantages of the invention will become apparent on reading the following description, given non-limitingly and which refers to the appended drawings, in which.

PROCESS FOR PREPARING A COMPOSITION ACCORDING TO THE INVENTION

Figure 1:
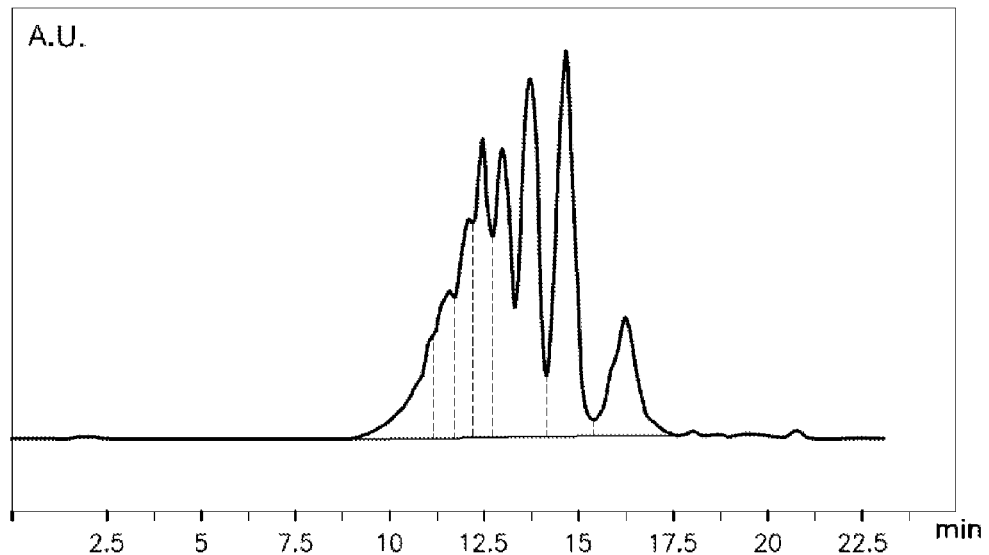
FIG. 1 is a chromatogram representing an analysis of a peptide composition according to the invention by gel filtration.

Skins of temperate-water fish are removed or purchased, especially from fish of the family Pangasiidae—especially *Pangasius hypophtalmus* (or *Pangasianodon hypophtalmus*), *Pangasius pangasius, Pangasius bocourti*—and/or from catfish or from the family Cichlidae—especially from the genus *Oreochromis*, in particular *Oreochromis niloticus* or from the genus *Tilapia*.

A succession of steps of washing the skin, acid treatment of the washed skin and extraction and purification of the collagen are carried out. A step of enzymatic hydrolysis of the collagen from the fish skins thus obtained is then carried out so as to form the composition according to the invention. For this purpose, water is heated to a temperature of between 70° C. and 75° C. A weight of collagen from fish skins is gradually poured into the hot water, with stirring, such that the proportion by weight of collagen in the water is 45%, and the pH of the solution is adjusted to pH 6.0. An amount of cysteine protease of plant origin is then added to the solution of re-melted collagen. As cysteine protease, at least one protease of *Carica papaïa* is chosen, especially lypaine (Lypaine®, LYVEN, Collombelles, France) in the dry state. The weight ratio of cysteine protease to the weight of collagen is adapted depending on the desired hydrolysis conditions. For example, the weight ratio of cysteine protease to the weight of collagen is 0.2%. The temperature of the solution is kept at a value of between 65° C. and 70° C., adapted to promote the enzymatic activity of the cysteine protease and to maintain the optimum fluidity of the collagen hydrolyzate, taking into account the fact that the viscosity of the collagen hydrolyzate decreases with the hydrolysis time. The solution is kept at this temperature for a duration of the order of 45 minutes.

The enzymatic hydrolysis reaction is stopped by heating the collagen hydrolyzate to a temperature greater than the denaturation temperature of the cysteine protease, for example to a temperature of between 85° C. and 90° C. for 20 minutes. The hydrolyzate of collagen from fish skins is optionally subjected to a step of filtration then to a step of pasteurization for a duration of at least 2 minutes at a pasteurization temperature of between 85° C. and 90° C. at least.

The hydrolyzate of collagen or collagen peptides is then subjected to a step of drying under conditions suitable for forming a composition according to the invention, formed of a powder of predetermined particle size.

Structural Characterizations of the Peptides of the Composition According to the Invention Amino Acid Composition A characterization of the composition of peptides resulting from the hydrolysis of collagen from skins of temperate-water fish according to the invention is carried out by assaying the free and total amino acids using an amino acid analyzer or using high performance liquid chromatography (HPLC) equipment in accordance with standard ISO 13903:2005. By way of comparison, the amino acid composition of a hydrolyzate of collagen from skins of cold-water fish (Alaska pollock), taken from deep water of the Bering Sea (Alaska) is determined. The comparative results are presented in table 6 below.

TABLE 6

| Amino acid, mol % | Collagen from temperate-water fish according to the invention | Collagen from cold-water fish, for comparison |
| --- | --- | --- |
| Glycine | 20.0-24.5 | 25.1-34.7 |
| Alanine | 7.3-11.3 | 8.6-10.9 |
| Proline | 10.6-14.6 | 8.4-9.8 |
| Glutamic acid | 8.0-13.0 | 4.2-6.8 |
| Serine | 1.5-5.5 | 6.3-8.6 |
| Arginine | 6.9-10.9 | 6.2-10.3 |
| Hydroxyproline | 6.0-12.0 | 5.2-5.5 |
| Aspartic acid | 3.1-7.1 | 3.7-5.2 |
| Threonine | 0.7-4.7 | 3.3-3.7 |
| Lysine | 1.5-5.5 | 3.2-4.5 |
| Leucine | 0.6-4.6 | 1.8-3.6 |
| Valine | 0-0.40 | 1.6-2.9 |
| Histidine | 0-3.3 | 1.5-1.6 |
| Phenylalanine | 0.3-4.3 | 1.3-2.4 |
| Methionine | 0-2.5 | 1.2-2.9 |
| Isoleucine | 0-3.5 | 1.0-2.0 |
| Hydroxylysine | 0-3.5 | 0-0.9 |
| Tyrosine | 0-1.5 | 0.3-1.0 |
| Cysteine | 0-2.0 | 0 |
| Tryptophan | 0 | 0 |

A characterization of a peptide composition according to the invention by the distribution of the apparent molecular weights of the peptides, by the polarity of the peptides and by the hydrophobicity of the peptides is also carried out.

Analysis of the Apparent Molecular Weights of the Peptides

The distribution of apparent molecular weights of the peptides constituting a composition according to the invention is analyzed by gel permeation on a liquid chromatography column of dimensions 300×7.8 mm in which the stationary phase consists of a silica-based gel (BioSep-SEC-S2000, Phenomenex, Le Peck, France) with a porosity of 5 µm. The filtration column is kept at a temperature of 40° C. The mobile phase consists of a mixture comprising (A) ultrapure water with trifluoroacetic acid (0.1% by volume) added thereto and (B) acetonitrile (A/B; 75/25; v/v). The flow rate of the mobile phase is kept at 0.6 ml/min. The volume of the solution comprising the peptide composition to be analyzed is 25 µl. The detection is carried out at the outlet of the gel permeation column by measuring absorbance at a wavelength of 214 nm. In parallel, a calibration curve for determining an apparent molecular weight as a function of retention time is produced. In order to produce this calibration curve, known peptides of molecular weight of between 100 Da and 30 kDa are chosen. The known standards are proline, glutathione, ribonuclease A and trypsin, of respective apparent molecular weights of 115 Da, 307 Da, 13.7 kDa and 28.2 kDa.

The apparent molecular weights and the retention times expressed in minutes of the standards are given in table 1 below:

TABLE 1

| Standard | MW, Da | Retention time, min |
| --- | --- | --- |
| Proline | 115 | 17.193 |
| Glutathione | 307 | 16.938 |
| Ribonuclease A | 13 700 | 10.275 |
| Trypsin | 28 161 | 10.232 |

The peptides are eluted from the column in succession as a function of their decreasing apparent molecular weight. The retention time values of each family of peptides of the composition to be analyzed, corresponding to a peak on the chromatogram, are read off at the top of each peak of the chromatogram and converted into an apparent molecular weight value by comparison with the calibration curve. The relative values of the amounts of each family of peptides correspond to the value of the area under the curve corresponding to each peak of the chromatogram. These values are expressed by the ratio of the value of the area under the curve corresponding to a family of peptides to the sum of the area values of each family of peptides.

The values of retention time (min), corresponding apparent molecular weights (Da) and percentage of the area under the curve (expressed as percentage of the total area under the curve) corresponding to each family of peptides of the chromatogram shown in FIG. 1 are given in table 2 below. Each group of peptides corresponding to a peak on the chromatogram is identified by the apparent molecular weight value corresponding to the maximum of this peak on the chromatogram.

TABLE 2

| Retention time (min) | Apparent molecular weight (Da) | Area under the curve (%) |
|---|---|---|
| 11.130 | 10 869 | 6.6 |
| 11.560 | 8096 | 7.0 |
| 12.072 | 5703 | 9.6 |
| 12.430 | 4461 | 13.0 |
| 12.962 | 3100 | 13.6 |
| 13.678 | 1897 | 19.0 |
| 14.638 | 983 | 21.6 |
| 16.217 | 333 | 9.6 |

The proportion of peptides of the composition according to the invention—the chromatogram of which is shown in FIG. 1 and the values of which are given in table 2—for which the apparent molecular weight is less than 1400 Da is 31.2% (apparent molecular weights with values 983 Da and 333 Da) relative to all the peptides of the composition.

The mean apparent molecular weight of the peptides of the composition according to the invention, the apparent molecular weight values of which are given in table 2, is 3442 Da. The mean apparent molecular weight of the peptides of the composition is defined as the mean of the weighted apparent molecular weight values corresponding to each group of peptides of the composition corresponding to the same peak on the chromatogram. The weighted apparent molecular weight value of a group of peptides of the same peak on the chromatogram corresponds to the apparent molecular weight value at the top (maximum) of the peak, weighted by the ratio of the value of the area under the curve of the corresponding peak to the (total) area under the curve of the chromatogram. "Area under the curve" or "area under the peak" is intended to mean the area of the space between the curve tracing the peak of the chromatogram and the baseline of the chromatogram. In particular, the area under one of the peaks of the chromatogram extends between two minima of the curve of the chromatogram, enclosing a top (or maximum) of the curve of the chromatogram.

By way of generalization, table 3 below presents the mean values of the retention times (min), of the corresponding apparent molecular weights (Da) and of the percentage of the area under the curve for each family of peptides, corresponding to separate analyses of three peptide compositions according to the invention.

TABLE 3

| Retention time (min) | Molecular weight (Da) | Area (%) |
|---|---|---|
| 11.13 ± 0.15 | 10 870 ± 830 | 4.6 ± 2 |
| 11.50 ± 0.20 | 8596 ± 700 | 5.6 ± 2 |
| 11.7 ± 0.1 | 7180 ± 100 | 4.5 ± 1 |
| 12.27 ± 0.3 | 5703 ± 400 | 9.6 ± 2 |
| 12.45 ± 0.20 | 4430 ± 100 | 13.0 ± 1 |
| 13.00 ± 0.06 | 3100 ± 100 | 13.5 ± 1 |
| 13.67 ± 0.06 | 1870 ± 40 | 20.0 ± 1 |
| 14.64 ± 0.02 | 983 ± 20 | 22.5 ± 2 |
| 16.18 ± 0.04 | 340 ± 10 | 12.0 ± 2.5 |
| 16.79 ± 0.01 | 224 ± 5 | 0.7 ± 0.15 |

The mean proportion of peptides of compositions according to the invention—the values of which are given in table 3—and the molecular weight of which is less than 1400 Da is 35.2% (essentially corresponding to the apparent molecular weights of 983 Da and 340 Da).

Analysis of the Polarity of the Constituent Peptides

The proportion of anionic peptides in the composition according to the invention, the distribution of the apparent molecular weights of which is given in table 2, is analyzed, that is to say the proportion of peptides having a negative charge at pH 8.35. The proportion of neutral and/or cationic peptides in the composition according to the invention is also analyzed, that is to say the proportion of peptides having an overall neutral charge at pH 8.35, or having a positive charge at pH 8.35. Such an analysis is carried out by ion exchange high performance liquid chromatography (HPLC), in which the stationary phase is an anion exchange resin (Hydrophase HP-SAX, Interchim, Montlugon, France) with a particle size of 10 μm. The ion exchange HPLC chromatography column is of dimensions 100×7.8 mm.

The HPLC chromatographic column is conditioned by ion exchange in a tris(hydroxymethyl)aminomethane (Tris) buffer at a concentration of 5 mM in water and the pH of which is adjusted to the value of 8.35.

The temperature of the column is kept at a temperature of 25° C. The flow rate of the mobile phase in the column is 1 ml/min. A sample of the peptide composition to be analyzed is prepared such that the concentration thereof is 2 g/l, by dilution in ultrapure water. A volume of 90 μl of this solution to be analyzed is introduced at the top of the column. The detection is carried out by continuously measuring the absorbance at 214 nm.

Starting from the introduction of the sample at the top of the column, the mobile phase consists of 5 mM Tris at pH 8.35 (solution A) for a duration of 7 minutes, then of a mobile phase in which a solution B, formed of 5 mM Tris, 5 M NaCl, pH 8.35, increases linearly from 0 to 100% in solution A in 30 minutes. The elution is then maintained by solution B for 2 minutes.

Figure 2:
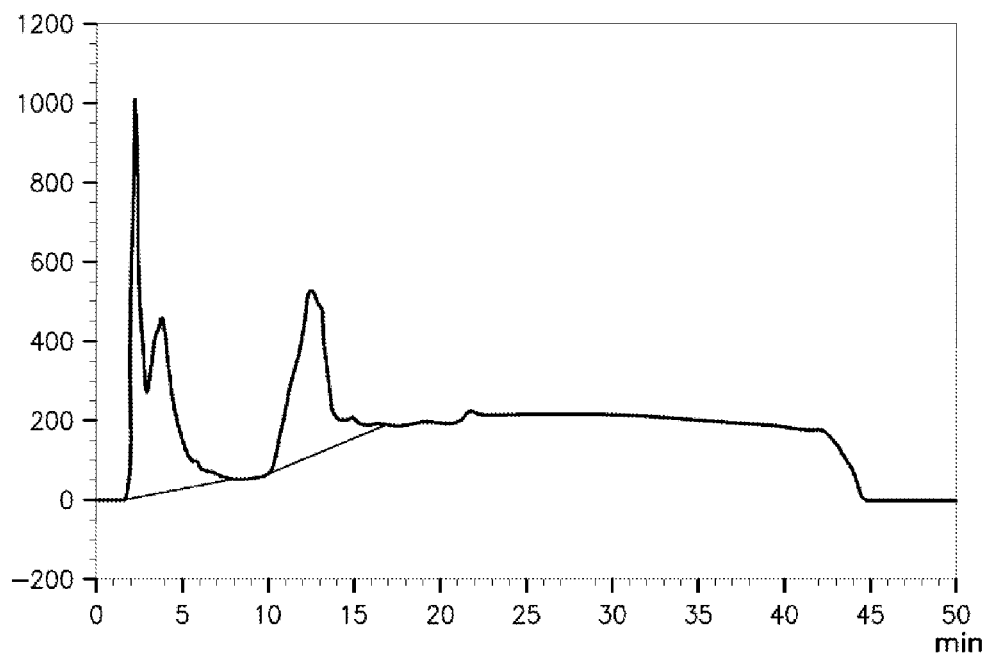
FIG. 2 is a chromatogram representing an HPLC analysis of a peptide composition according to the invention on an anion exchange resin.

The chromatogram obtained is shown in FIG. 2. The anionic peptides leave the column with a retention time of between 10 min and 17.5 min corresponding to an NaCl concentration of between 0.5 M and 1.7 M. The proportion of anionic peptides in the peptide composition according to the invention, the analysis of which is shown in FIG. 2, is 36.9%. The neutral and cationic peptides leave the column with a retention time of between 1 minute and 8 minutes. The proportion of neutral and cationic peptides in the peptide composition according to the invention, the analysis of which is shown in FIG. 2, is 57.5%.

By way of generalization, this analysis is reproduced on three peptide compositions according to the invention. The mean proportion of anionic peptides in these compositions according to the invention is between 27.9% and 42.5% and the mean proportion of neutral and cationic peptides in these compositions according to the invention is between 57.5% and 72.1%.

Analysis of the Hydrophobicity of the Constituent Peptides

The hydrophobicity of the constituent peptides of the composition according to the invention is analyzed by reversed-phase liquid chromatography on a column of silica grafted with butyl groups (Vydac 214TP™ $C_4$, Grace, Epernon, France), of dimensions 250×4.6 mm. The particle size of the silica is 5 µm and the porosity thereof is 300 Å.

The column is conditioned in ultrapure water acidified with 0.1% of trifluoroacetic acid. The temperature of the column is kept at a temperature of 40° C. The flow rate of the mobile phase in the column is 0.6 ml/min. A sample of the peptide composition to be analyzed is prepared such that the concentration thereof is 2 µg/l, by dilution in ultrapure water. A volume of 100 µl of this solution to be analyzed is introduced at the top of the column. Detection is carried out by continuously measuring the absorbance at 214 nm.

Starting from the introduction of the sample at the top of the column, the mobile phase consists of acidified water (solution A) for a duration of 7 minutes, then of a mobile phase in which a solution B, formed of water acidified with 0.1% (by volume) of trifluoroacetic acid and comprising 40% of acetonitrile increases linearly from 0 to 100% in solution A in 30 minutes.

Figure 3:
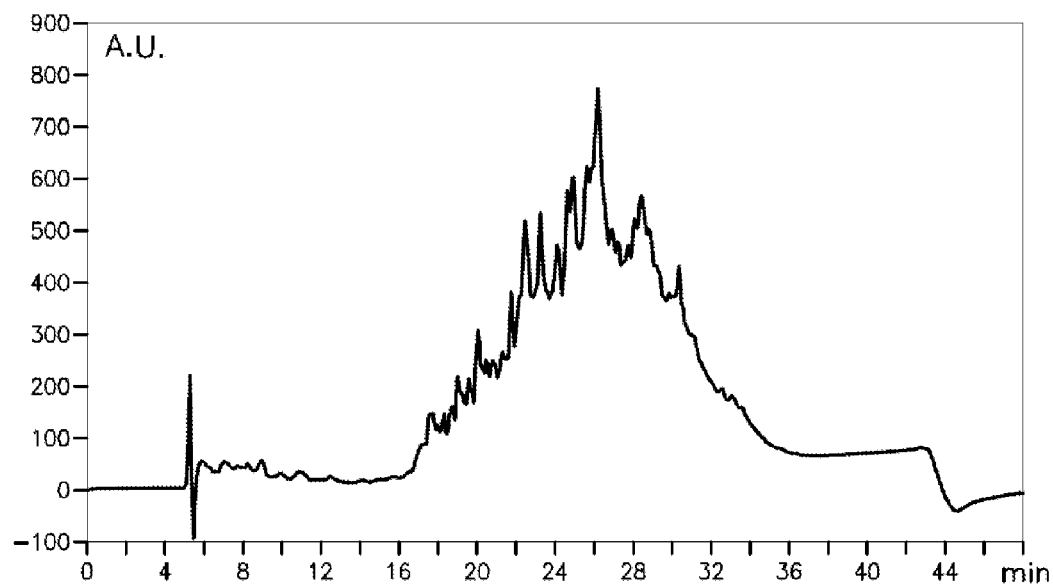
FIG. 3 is a chromatogram representing an analysis of a peptide composition according to the invention by reversed-phase chromatography.

The chromatogram obtained is shown in FIG. 3. The peptides of the composition according to the invention leave the column with a retention time of between 16 min and 36 min corresponding to a percentage of acetonitrile of between 12% and 38% in the eluent. The median retention time of the peptides of the composition according to the invention is 26 min, corresponding to a percentage of acetonitrile of 25% in the eluent.

Biological Effects of a Composition According to the Invention

Effect on Colonization by *Candida albicans* and on Digestive Candidiasis

The effect of a composition according to the invention on digestive candidiasis induced in female C57BL/6 mice, aged 8 weeks and of a weight of between 20-25 g is analyzed. These mice are fed for a duration of 21 days with the composition according to the invention at an amount of 4 g/kg/day. On the $21^{st}$ day, digestive candidiasis is induced by force-feeding each mouse with an amount of $5\times10^7$ yeast cells. Between 2 days (D2) and 7 days (D7) after induction, the mice's stools are collected and the yeast load is evaluated (CFU/mg of stools) on a chromogenic medium. The results are given in table 4 below in comparison with the values measured on mice in which digestive candidiasis is induced but which are not treated with the composition according to the invention.

TABLE 4

| Day after induction | Composition according to the invention | CFU/mg stools |
|---|---|---|
| D 3 | Yes | 125 |
| D 3 | No | 263 |
| D 4 | Yes | 125 |
| D 4 | No | 275 |
| D 5 | Yes | 150 |
| D 5 | No | 250 |

The composition according to the invention induces a reduction in the load of *Candida albicans*.

Anti-Inflammatory Peptide Composition According to the Invention

A comparative analysis is carried out of the stimulation of expression of inflammatory type 1 macrophage (M1) receptors and/or anti-inflammatory type 2 macrophage (M2) receptors by a composition of peptides according to the invention resulting from an enzymatic hydrolysis of collagen from skins of temperate-water fish and by a composition of peptides resulting from an enzymatic hydrolysis of collagen from skins of cold-water fish (outside the invention).

Macrophages/monocytes from healthy human subjects were cultured for 24 hours in the presence of a pretreatment composition (control without collagen peptides, invention, outside of the invention, table 7) at a concentration of 100 µg/ml of culture medium. The effect of this pretreatment on the expression of characteristic receptors of type 1 macrophages (M1, inflammatory) and on the expression of characteristic receptors of type 2 macrophages (M2, anti-inflammatory) is evaluated by the level of production of oxygen free radicals (reactive oxygen species, ROS) by the receptors of type 1 macrophages specifically stimulated by a phorbol ester ("12-myristate-13-acetate-phorbol, TPA") at a concentration of 100 µM or by the receptors of type 2 macrophages specifically stimulated by non-opsonized zymosan (NOZ) at a concentration of 100 µg/ml. The level of production of oxygen free radicals is measured by chemiluminescence in the presence of luminol at a concentration of 66 µM. The results presented in table 7 below represent the mean values obtained with three assays.

TABLE 7

| | | Luminescence, arbitrary units $\times 10^{-8}$ | | |
|---|---|---|---|---|
| | | Pretreatment | | |
| | | Without collagen | invention | Outside the invention |
| Inducer | Not induced | 1.23 ± 0.16 | 1.64 ± 0.10 | 1.80 ± 0.18 |
| | NOZ | 4.49 ± 0.43 | 5.06 ± 0.02 | 3.91 ± 0.38 |
| | TPA | 9.96 ± 0.40 | 6.75 ± 0.11 | 1.4 ± 0.59 |

It is observed that the macrophages/monocytes not treated (not induced) by NOZ and TPA have a level of production of oxygen free radicals that is substantially constant depending on the nature of the pretreatment (without collagen, according to the invention and outside the invention).

The macrophages/monocytes pretreated with a composition of peptides according to the invention, that is to say resulting from an enzymatic hydrolysis of collagen from skins of temperate-water fish, have an increased expression of the receptors of anti-inflammatory type 2 macrophages (M2) revealed by the chemiluminescence intensity (5.06× $10^8$ AU) induced by NOZ, compared to the macrophages/monocytes pretreated with a composition of peptides outside the invention, that is to say resulting from an enzymatic hydrolysis of collagen from skins of cold-water fish (3.91× $10^8$ AU).

The macrophages/monocytes pretreated with a composition of peptides according to the invention, that is to say resulting from an enzymatic hydrolysis of collagen from skins of temperate-water fish, have a decreased expression of the receptors of inflammatory type 1 macrophages (M1) revealed by the chemiluminescence intensity (6.75×$10^8$ AU) induced by TPA, compared to the macrophages/monocytes pretreated with a composition of peptides outside the invention, that is to say resulting from an enzymatic hydrolysis of collagen from skins of cold-water fish ($1.49 \times 10^9$ AU) The peptide composition according to the invention has an anti-inflammatory phenotype compared to a composition of peptides outside the invention, that is to say resulting from an enzymatic hydrolysis of collagen from skins of cold-water fish, by increasing the level of expression of the receptors of anti-inflammatory type 2 macrophages (M2) and by decreasing the level of expression of the receptors of inflammatory type 1 macrophages (M1).

The preparation of a composition of peptides according to the invention resulting from skins of temperate-water fish and having an aminogram in which:
- glycine is in a molar amount such that the ratio of this amount to the sum of the molar amounts of the amino acids in the composition is between 20.0% and 24.5%;
- hydroxyproline is in a molar amount such that the ratio of this amount to the sum of the molar amounts of the amino acids in the composition is between 6.0% and 12.0%;
- proline is in a molar amount such that the ratio of this amount to the sum of the molar amounts of the amino acids in the composition is between 10.6% and 14.6%;

has such an anti-inflammatory phenotype, confirmed by mice colonic inflammation assays on a murine model, which is not found with a composition of peptides resulting from skins of cold-water fish and having an aminogram as described in table 6.

Colonic Inflammation in a Murine Model

The anti-inflammatory effect of the peptide composition according to the invention is demonstrated on a murine model of pharmacological inflammation induced by dextran sulfate sodium (DSS, MP Biomedical LLC, Canada) characterized by weight loss and bloody diarrhea.

The effect of the peptide composition according to the invention in limiting the weight loss of mice treated with DSS was studied. Female C57BL/6 laboratory mice aged from 10 to 11 weeks and of a weight of between 20 and 25 grams were treated for 7 days ($D_1$ to $D_7$) with DSS dissolved at an amount of 1.5% (weight/volume) in the mice's drinking water. These mice are also treated for 12 days ($D_1$ to $D_{12}$) with the composition according to the invention at an amount of 0.1 g/kg/day; 1 g/kg/day and 4 g/kg/day. This amount of composition according to the invention is dispensed in the drinking water of the mice. On $D_{12}$, the mice are euthanized.

5 batches of mice are prepared, each batch containing 10 mice, in which:
- batch 1 is treated with DSS for 7 days;
- batch 2 is treated with DSS for 7 days and with the composition according to the invention at an amount of 0.1 g/kg/day for 12 days;
- batch 3 is treated with DSS for 7 days and with the composition according to the invention at an amount of 1 g/kg/day for 12 days;
- batch 4 is treated with DSS for 7 days and with the composition according to the invention at an amount of 4 g/kg/day for 12 days;
- batch 5 is treated with DSS for 7 days and with hydrolyzed casein not in accordance with the invention at an amount of 0.1 g/kg/day for 12 days.

In parallel, a control is carried out on 5 mice which are not treated with DSS and for which inflammation is not induced, and which are not treated with a peptide composition according to the invention.

1. Study of Body Weight

Figure 4:
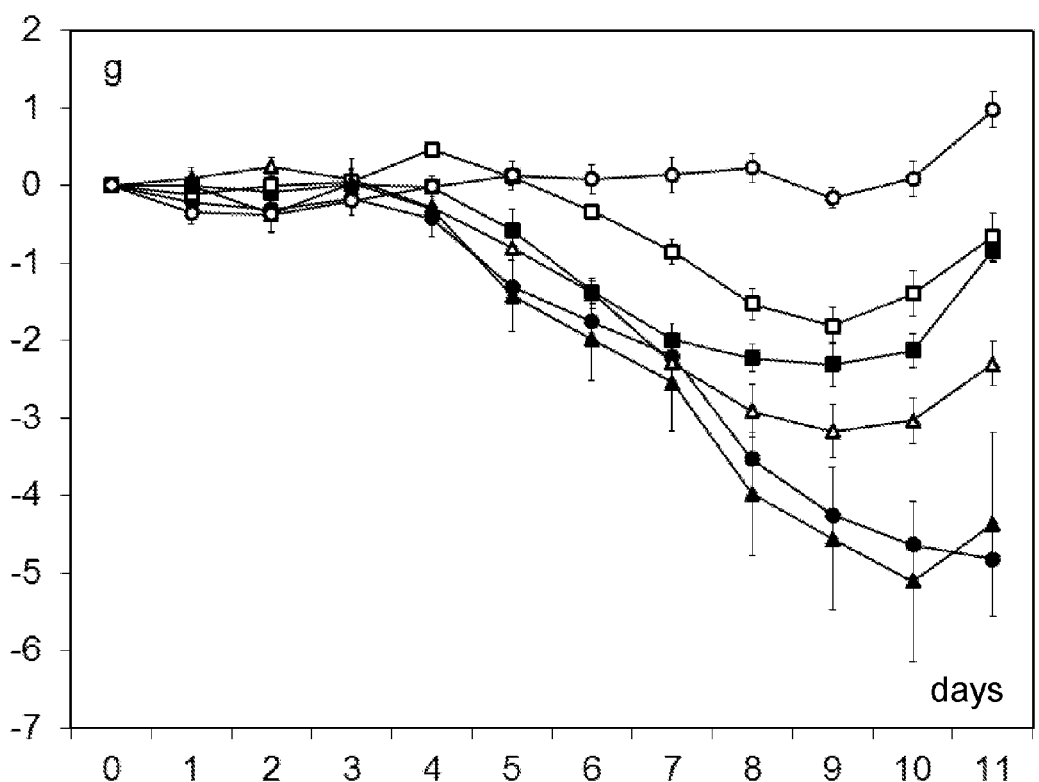
FIG. 4 is a graphical depiction representing the change in the body mass of mice in which colonic inflammation has been induced by dextran sulfate sodium (DSS)

The weight of each mouse is measured each day and the weight loss undergone by each mouse from each batch is calculated. The results are presented in FIG. 4, in which the control is represented by empty circles (○), batch 1 is represented by filled-in circles (●), batch 2 is represented by empty squares (□), batch 3 is represented by filled-in squares (■), batch 4 is represented by empty triangles (Δ) and batch 5 is represented by filled-in triangles (▲). It is observed that, from 0.1 g/kg/day (batch 2, □), the composition according to the invention limits the mice's weight loss. This limiting is also observed for 1 g/kg/day (batch 3, ■) and for 4 g/kg/day (batch 4, Δ). It is not observed for the treatment with hydrolyzed casein (batch 5, ▲), for which the weight loss is comparable to the weight loss of the mice from batch 1 (●).

The composition according to the invention makes it possible to limit, or even to virtually entirely do away with, the weight loss caused by the inflammation induced by the dextran sulfate sodium (DSS) in mice. The composition according to the invention is capable of being used as medicament, especially for the treatment of colonic inflammation.

2. Histology

The transversal histological sections of colons from mice treated with DSS alone exhibit, after bichromatic staining with hematoxylin and eosin, significant infiltrations of inflammatory cells at the mucosa and sub-mucosa. The thickness of the epithelium is reduced. The epithelium exhibits extensive ulceration. The transversal histological sections of colons from mice treated with DSS and with the composition according to the invention at an amount of 0.1 g/kg/day, 1 g/kg/day and 4 g/kg/day exhibit, after bichromatic staining with hematoxylin and eosin, tightly packed, straight tubular glands representative of a healthy and functional epithelium.

3. Macroscopic Score

For each treatment condition, a macroscopic score is calculated from notation created according to the Wallace scale relating to the appearance of the stools, the damaged appearance of the colon, the weight of the colon and the length of the colon, according to the Wallace scale (E. S. Kimball, N. H. Wallace, C. R. Schneider, M. R. D'Andrea and P. J. Hornby; 2004; Neurogastroenterol Motil; 16, 811-818. Vanilloid receptor 1 antagonists attenuate disease severity in dextran sulfate sodium-induced colitis in mice). The more inflammatory the colon is, the higher the value of the macroscopic score, and the healthier the colon is, the lower the value of the macroscopic score.

The mean values and the standard deviation of the macroscopic score of the mice from batches 1 to 5 are given in table 5 below.

TABLE 5

| | Mean macroscopic score | Standard deviation | |
|---|---|---|---|
| Batch 1 | 5.14 | 0.46 | |
| Batch 2 (0.1 g/kg/day) | 1.30 | 0.33 | $p < 0.01$ |
| Batch 3 (1 g/kg/day) | 1.90 | 0.5 | $p < 0.01$ |
| Batch 4 (4 g/kg/day) | 3.00 | 0.33 | $p < 0.01$ |
| Batch 5 | 5.00 | 0.61 | |

A reduction in the macroscopic score is observed, induced by treatment with the composition according to the invention, that is to say an improvement in the inflammatory state of the colon induced by the composition according to the invention.

4. Inhibition of the Expression of Pro-Inflammatory Markers in Mice

Figure 5:
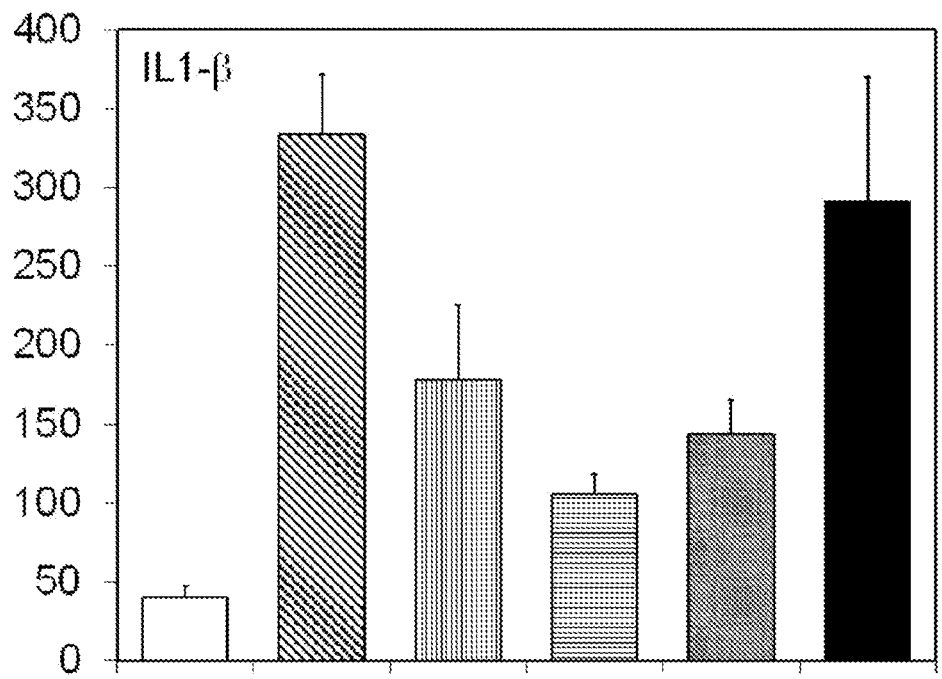
FIG. 5 is a graphical depiction in a histogram of the result of an IL-1β assay in the colon of mice by the ELISA method.
Figure 6:
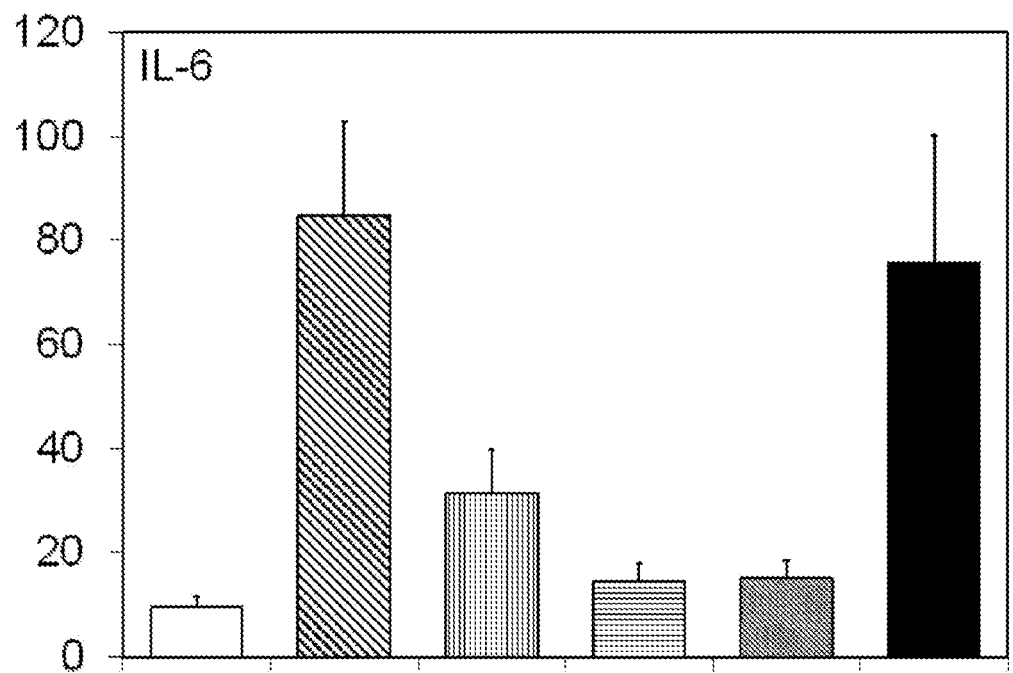
FIG. 6 is a graphical depiction in a histogram of the result of an IL-6 assay in the colon of mice by the ELISA method.
Figure 7:
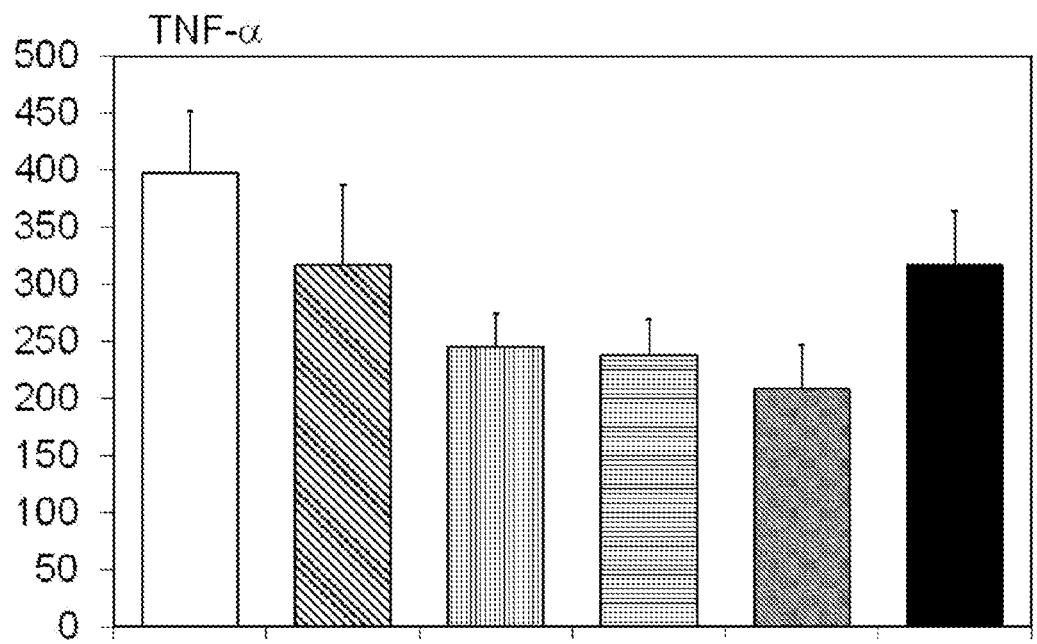
FIG. 7 is a graphical depiction in a histogram of the result of a TNF-α assay in the colon of mice by the ELISA method.

On $D_{12}$, the mice are euthanized and the level of expression at the colon of pro-inflammatory cytokines is assayed by the ELISA technique:

IL-1β: The level of IL-1β is analyzed by the ELISA technique and expressed in picograms (pg) of IL-1β per milligram (mg) of colon. The results are shown in FIG. 5, in which the first column (white column) corresponds to the analysis carried out on control mice. The second column (column with diagonal hatching) corresponds to the analysis carried out on the mice from batch 1. The third column (column with vertical hatching) corresponds to the analysis carried out on the mice from batch 4. The fourth column (column with horizontal hatching) corresponds to the analysis carried out on the mice from batch 3. The fifth column (gray column) corresponds to the analysis carried out on the mice from batch 2. The sixth column (black column) corresponds to the analysis carried out on the mice from batch 5. A statistically significant ($p<0.05$) reduction in the expression of IL-1β is observed in the colon of mice treated with the peptide composition according to the invention for doses of 0.1 g/kg/day, 1 g/kg/day and 4 g/kg/day compared to the colon of mice in which inflammation is induced by DSS and compared to mice in which inflammation is induced by DSS and treated with hydrolyzed casein. This effect was confirmed by analysis of IL-1β messenger RNA by quantitative RT-PCR in particular ($p<0.01$) for the doses of 0.1 g/kg/day and 1 g/kg/day;

IL6: The level of IL6 is analyzed by the ELISA technique and expressed in picograms (pg) of IL6 per milligram (mg) of colon. The results are shown in FIG. 6, in which the first column (white column) corresponds to the analysis carried out on control mice. The second column (column with diagonal hatching) corresponds to the analysis carried out on the mice from batch 1. The third column (column with vertical hatching) corresponds to the analysis carried out on the mice from batch 4. The fourth column (column with horizontal hatching) corresponds to the analysis carried out on the mice from batch 3. The fifth column (gray column) corresponds to the analysis carried out on the mice from batch 2. The sixth column (black column) corresponds to the analysis carried out on the mice from batch 5. A statistically significant reduction in the expression of IL6 is observed in the colon of mice treated with the peptide composition according to the invention for doses of 0.1 g/kg/day ($p<0.01$), 1 g/kg/day ($p<0.01$) and 4 g/kg/day ($p<0.05$) compared to the colon of mice in which inflammation is induced by DSS and compared to mice in which inflammation is induced by DSS and treated with hydrolyzed casein. This effect was confirmed by analysis of IL6 messenger RNA by quantitative RT-PCR;

TNF-α: The level of TNF-α is analyzed by the ELISA technique and expressed in picograms (pg) of TNF-α per milligram (mg) of colon. The results are shown in FIG. 7, in which the first column (white column) corresponds to the analysis carried out on control mice. The second column (column with diagonal hatching) corresponds to the analysis carried out on the mice from batch 1. The third column (column with vertical hatching) corresponds to the analysis carried out on the mice from batch 4. The fourth column (column with horizontal hatching) corresponds to the analysis carried out on the mice from batch 3. The fifth column (gray column) corresponds to the analysis carried out on the mice from batch 2. The sixth column (black column) corresponds to the analysis carried out on the mice from batch 5. A statistically significant reduction in the expression of TNF-α is observed in the colon of mice treated with the peptide composition according to the invention for doses of 0.1 g/kg/day ($p<0.05$), 1 g/kg/day ($p<0.05$) and 4 g/kg/day ($p<0.05$) compared to the colon of mice in which inflammation is induced by DSS and compared to mice in which inflammation is induced by DSS and treated with hydrolyzed casein.

The analysis by quantitative RT-PCR (reverse transcriptase polymerase chain reaction) of the messenger RNAs of MCP1 shows a statistically significant reduction in these mRNAs induced by DSS, in particular for the doses of 0.1 g/kg/day ($p<0.01$) and 1 g/kg/day ($p<0.05$) of peptide composition according to the invention.

Figure 17:
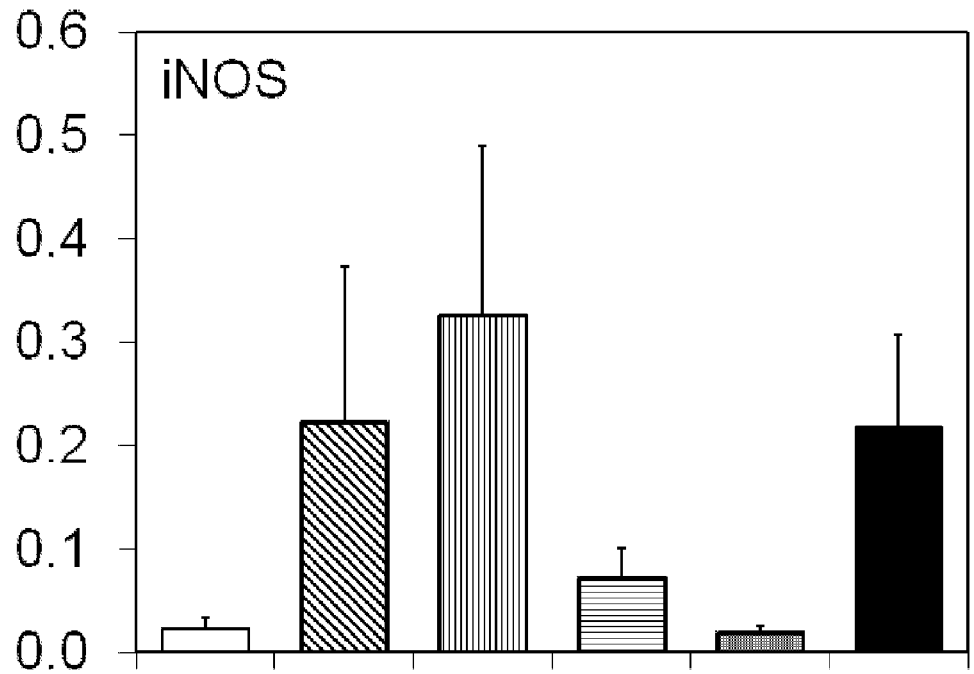
FIG. 17 is a graphical depiction in a histogram of an analysis by quantitative RT-PCR of the messenger RNA of inducible NO synthase (iNOS) in the colon of mice.

The analysis by quantitative RT-PCR (reverse transcriptase polymerase chain reaction) of the messenger RNAs of inducible NO synthase (iNOS) is shown in FIG. 17, in which the first column (white column) corresponds to the analysis carried out on control mice. The second column (column with diagonal hatching) corresponds to the analysis carried out on the mice from batch 1. The third column (column with vertical hatching) corresponds to the analysis carried out on the mice from batch 4. The fourth column (column with horizontal hatching) corresponds to the analysis carried out on the mice from batch 3. The fifth column (gray column) corresponds to the analysis carried out on the mice from batch 2. The sixth column (black column) corresponds to the analysis carried out on the mice from batch 5. A statistically significant reduction in the iNOS mRNAs induced by DSS is observed for doses of 0.1 g/kg/day ($p<0.05$) and 1 g/kg/day ($p<0.05$) of the peptide composition according to the invention.

5. Stimulation of the Expression of Anti-Inflammatory Markers in Mice

Figure 8:
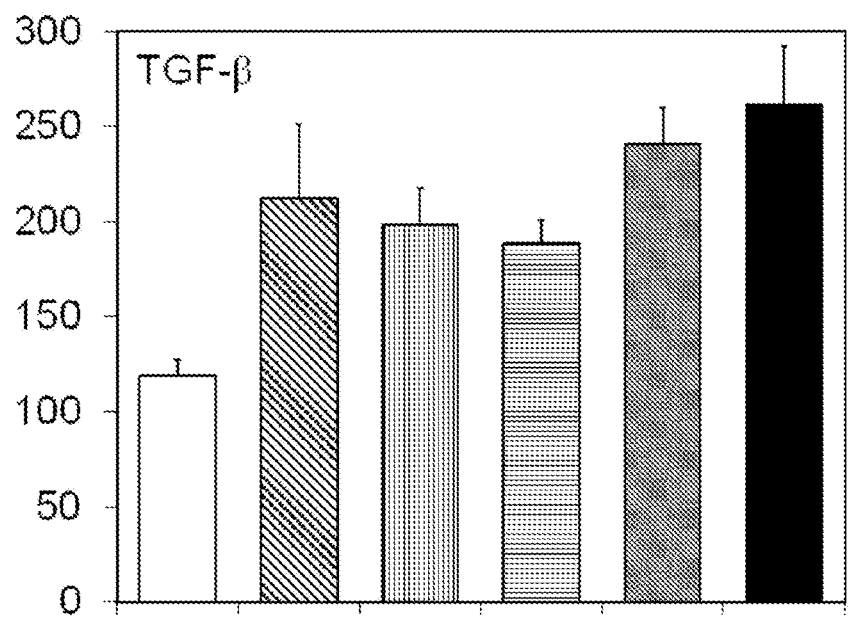
FIG. 8 is a graphical depiction in a histogram of the result of a TGF-β assay in the colon of mice by the ELISA method.
Figure 16:
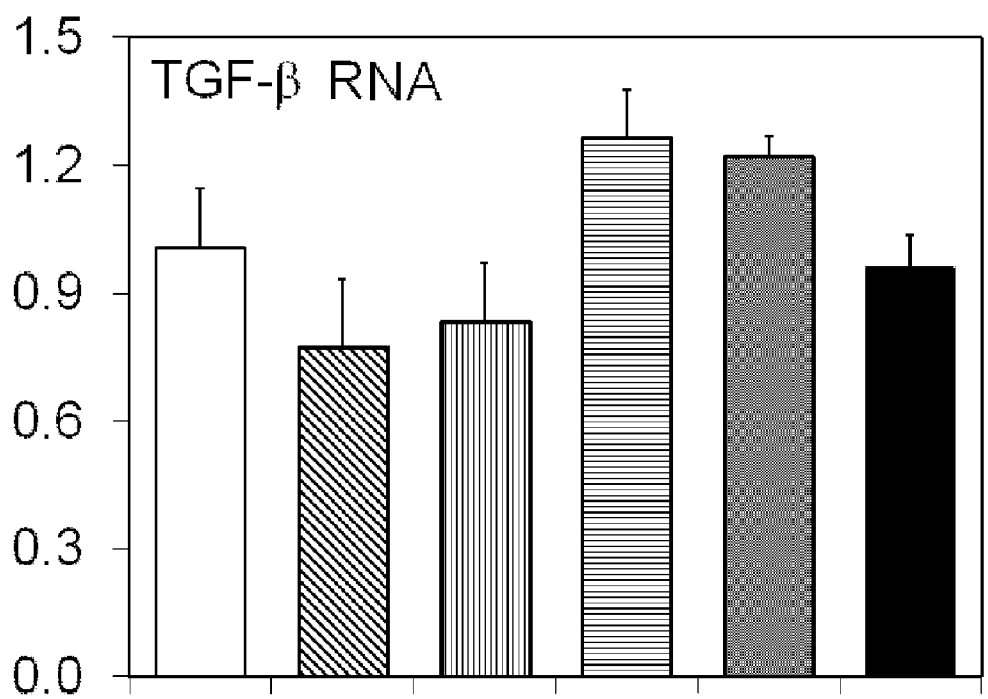
FIG. 16 is a graphical depiction in a histogram of an analysis by quantitative RT-PCR of the messenger RNA of TGF-β in the colon of mice.
Figure 18:
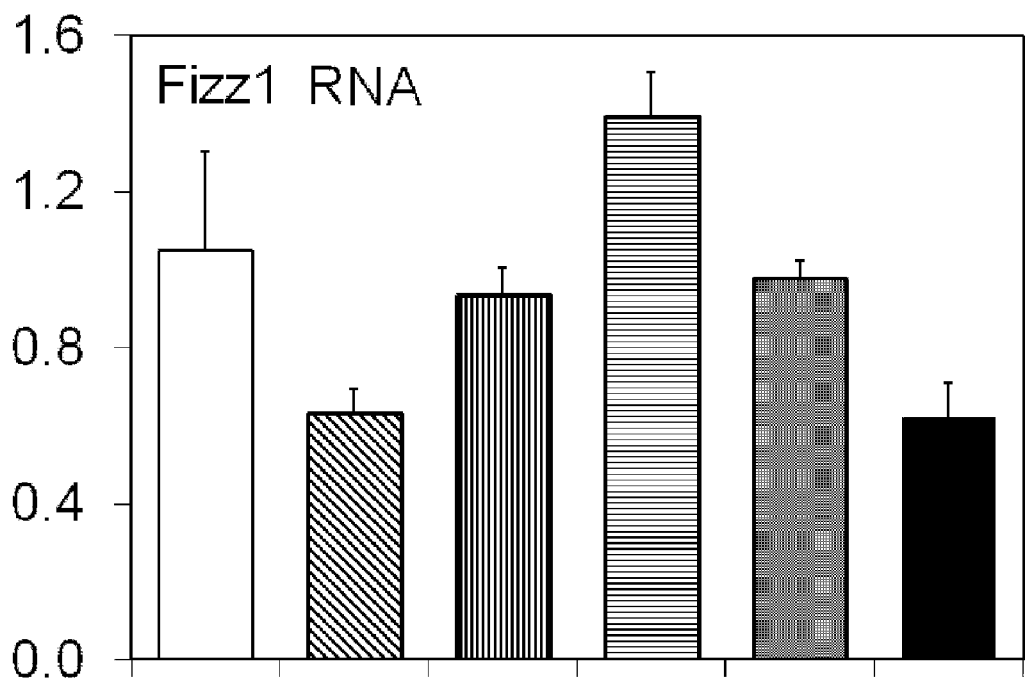
FIG. 18 is a graphical depiction in a histogram of an analysis by quantitative RT-PCR of the messenger RNA of Fizz1 in the colon of mice.

On $D_{12}$, the mice are euthanized and the level of expression at the colon of anti-inflammatory markers is assayed:

TGF-β: The level of TGF-β is analyzed by the ELISA technique and expressed in picograms (pg) of TGF-β per milligram (mg) of colon. The results are shown in FIG. 8, in which the first column (white column) corresponds to the analysis carried out on control mice. The second column (column with diagonal hatching) corresponds to the analysis carried out on the mice from batch 1. The third column (column with vertical hatching) corresponds to the analysis carried out on the mice from batch 4. The fourth column (column with horizontal hatching) corresponds to the analysis carried out on the mice from batch 3. The fifth column (gray column) corresponds to the analysis carried out on the mice from batch 2. The sixth column (black column) corresponds to the analysis carried out on the mice from batch 5. Stimulation of the expression of TGF-β is observed in the colon of mice treated with the peptide composition according to the invention for the dose of 0.1 g/kg/day compared to the colon of mice in which inflammation is induced by DSS. This effect was confirmed by analysis of TGF-β messenger RNA by quantitative RT-PCR, in particular for the doses of 0.1 g/kg/day and 1 g/kg/day of peptide composition according to the invention (FIG. 16);

Fizz1: Fizz1 is a marker of anti-inflammatory M2 macrophages. The analysis by quantitative RT-PCR (reverse transcriptase polymerase chain reaction) of the messenger RNAs of Fizz1 is shown in FIG. 18, in which the first column (white column) corresponds to the analysis carried out on control mice. The second column (column with diagonal hatching) corresponds to the analysis carried out on the mice from batch 1. The third column (column with vertical hatching) corresponds to the analysis carried out on the mice from batch 4. The fourth column (column with horizontal hatching) corresponds to the analysis carried out on the mice from batch 3. The fifth column (gray column) corresponds to the analysis carried out on the mice from batch 2. The sixth column (black column) corresponds to the analysis carried out on the mice from batch 5. A statistically significant increase in the Fizz1 messenger RNAs, decreased by DSS, is observed for doses of 0.1 g/kg/day ($p<0.05$), 1 g/kg/day ($p<0.01$) and 4 g/kg/day ($p<0.05$) of the peptide composition according to the invention;

a statistically significant increase in the Ym1 messenger RNAs, decreased by DSS, was also observed for doses of 0.1 g/kg/day ($p<0.05$) of the peptide composition according to the invention.

Figure 9:
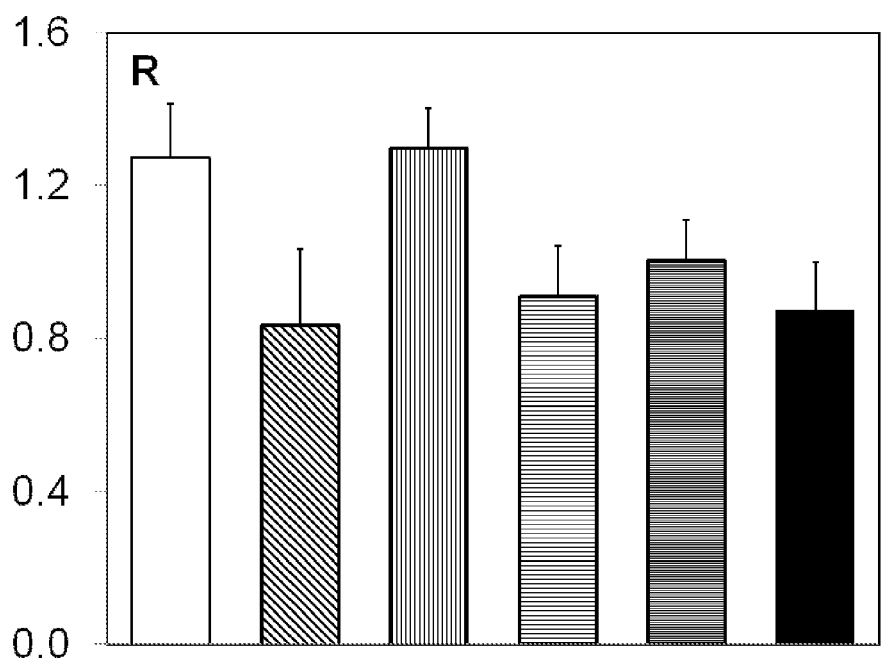
FIG. 9 is a graphical depiction in a histogram of the result of an assay by PCR of the fungal flora in the colon of mice.
Figure 10:
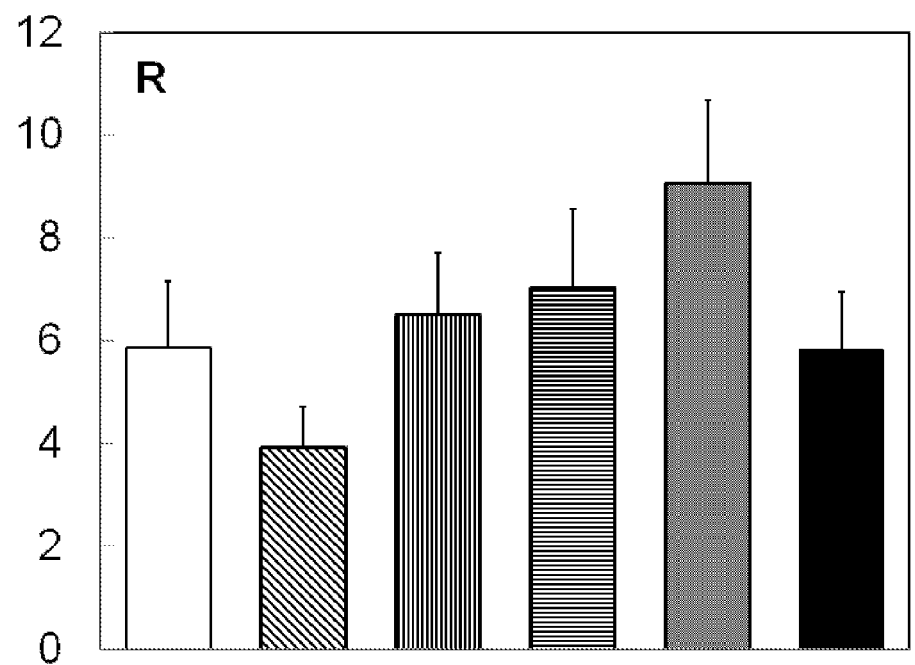
FIG. 10 is a graphical depiction in a histogram of the result of an assay by PCR of *Saccharomyces cerevisiae* in the colon of mice.
Figure 11:
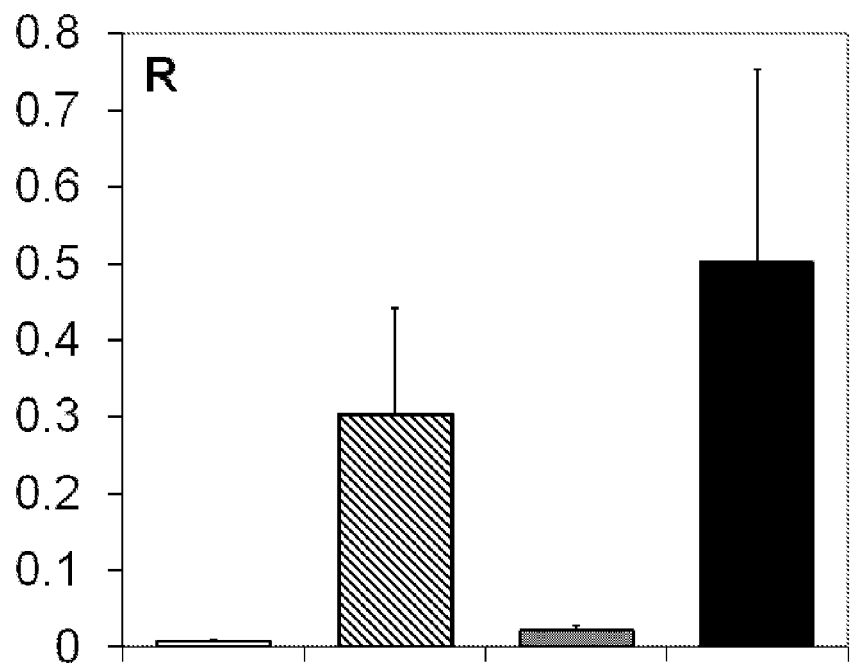
FIG. 11 is a graphical depiction in a histogram of the result of an assay by PCR of the Enterobacteriaceae in the colon of mice.
Figure 12:
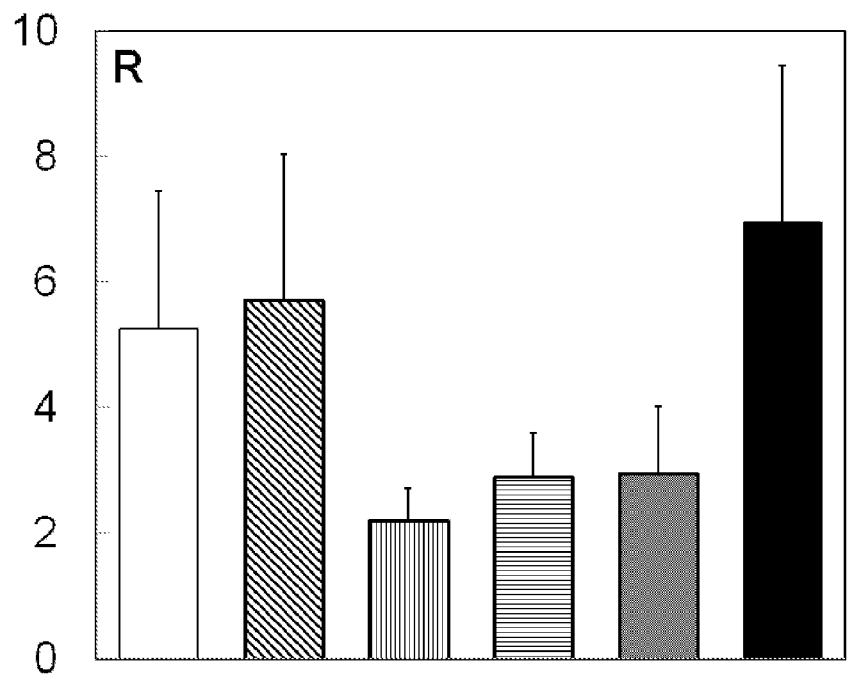
FIG. 12 is a graphical depiction in a histogram of the result of an assay by PCR of the Firmicutes in the colon of mice.
Figure 13:
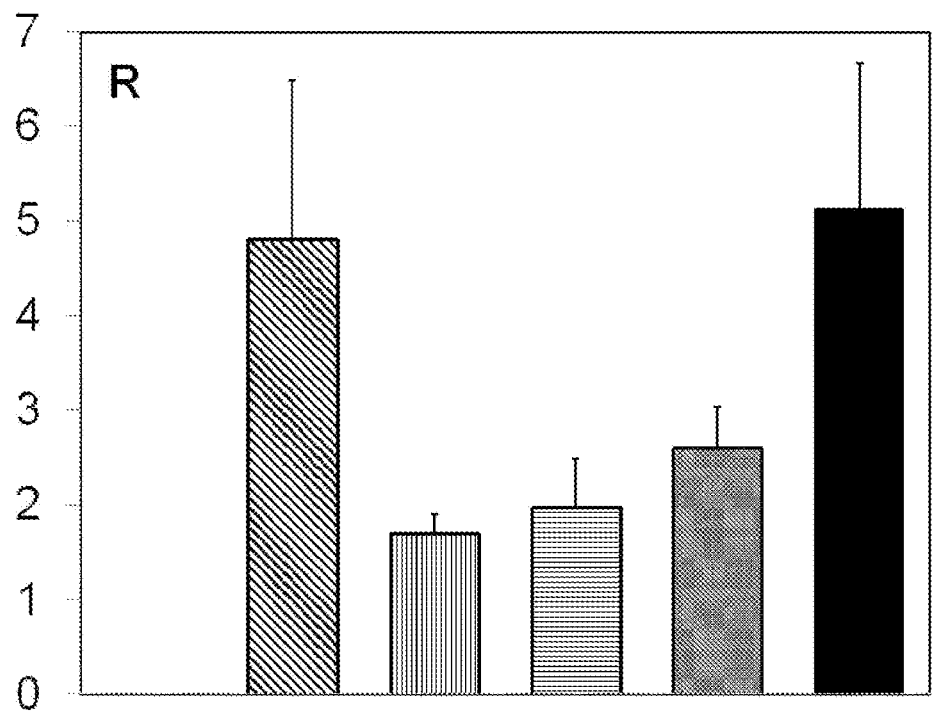
FIG. 13 is a graphical depiction in a histogram of the result of an assay by PCR of the Bacteroidetes in the colon of mice.
Figure 14:
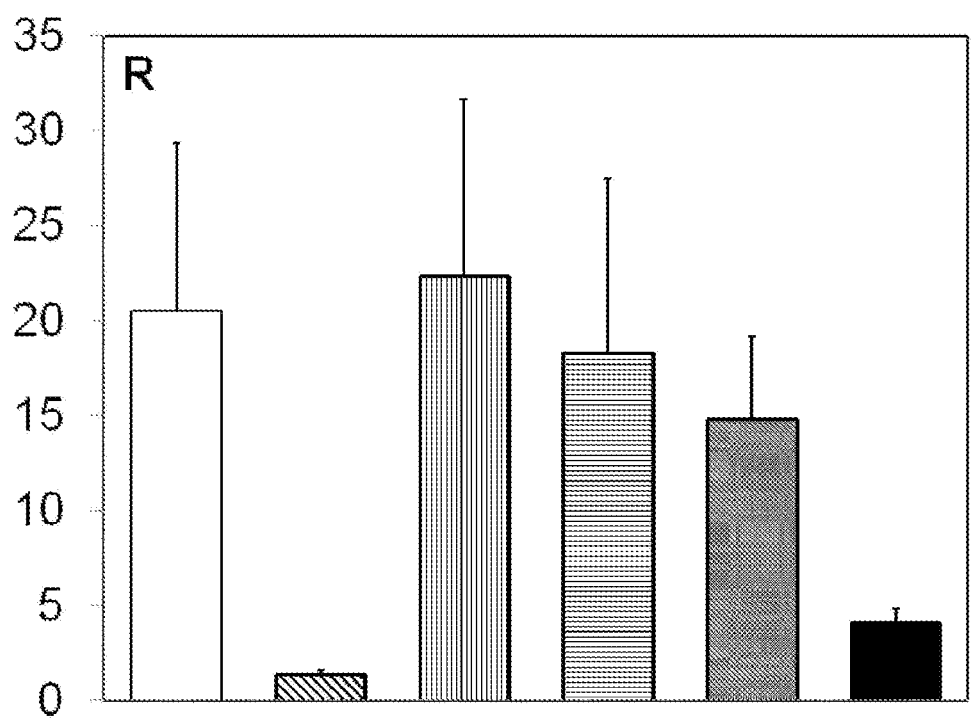
FIG. 14 is a graphical depiction in a histogram of the result of an assay by PCR of *Faecalibacterium prausnitzii* in the colon of mice.
Figure 15:
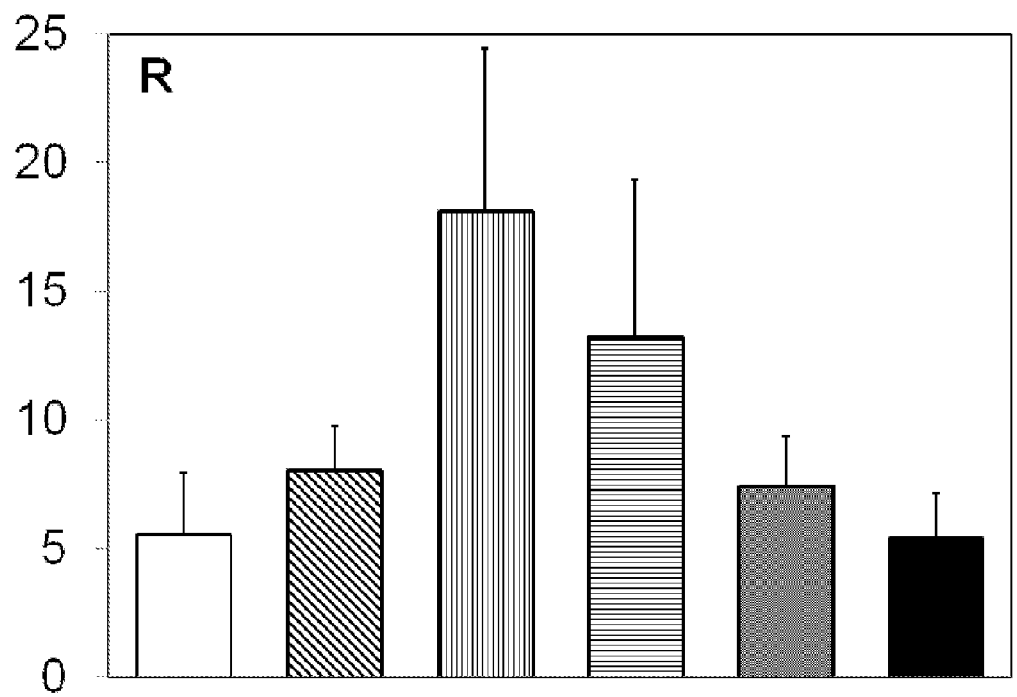
FIG. 15 is a graphical depiction in a histogram of the result of an assay by PCR of *Lactobacillus murinus* in the colon of mice.

6. Effect of the Peptide Composition According to the Invention on the Colonic Flora—Colon Microbiota On $D_{12}$, the mice are euthanized and the colonic flora of these mice is quantified by PCR (polymerase chain reaction). The values are standardized relative to the total amount of bacteria or fungi and relative to β-actin. β-actin constitutes the reference gene enabling standardization relative to the amount of colonic tissue analyzed. In particular, the following are quantified:

the total fungal flora by quantitative amplification of the ITS1-2 fungal ribosomal DNA. The ratio R of the amount of ITS1-2 fungal ribosomal DNA to the amount of β-actin DNA is shown in FIG. 9, in which the first column (white column) corresponds to the assay carried out on control mice. The second column (column with diagonal hatching) corresponds to the assay carried out on the mice from batch 1. The third column (column with vertical hatching) corresponds to the assay carried out on the mice from batch 4. The fourth column (column with horizontal hatching) corresponds to the assay carried out on the mice from batch 3. The fifth column (gray column) corresponds to the assay carried out on the mice from batch 2. The sixth column (black column) corresponds to the assay carried out on the mice from batch 5. The peptide composition according to the invention restores the fungal flora in particular at the dose of 4 g/kg/day;

the yeast *Saccharomyces cerevisiae* by quantitative amplification of the 26S ribosomal DNA. The ratio R of the amount of 26S ribosomal DNA to the amount of β-actin DNA is shown in FIG. 10. The first column (white column) corresponds to the assay carried out on control mice. The second column (column with diagonal hatching) corresponds to the assay carried out on the mice from batch 1. The third column (column with vertical hatching) corresponds to the assay carried out on the mice from batch 4. The fourth column (column with horizontal hatching) corresponds to the assay carried out on the mice from batch 3. The fifth column (gray column) corresponds to the assay carried out on the mice from batch 2. The sixth column (black column) corresponds to the assay carried out on the mice from batch 5. The peptide composition according to the invention statistically significantly restores the *Saccharomyces cerevisiae* flora at doses of 0.1 g/kg/day ($p<0.05$), 1 g/kg/day ($p<0.05$) and 4 µg/kg/day ($p<0.05$). In this instance, *S. cerevisiae* has anti-inflammatory potential;

the Enterobacteriaceae flora by quantitative amplification of the 16S ribosomal DNA. The ratio R of the amount of 16S ribosomal DNA to the amount of β-actin DNA is shown in FIG. 11. The first column (white column) corresponds to the assay carried out on control mice. The second column (column with diagonal hatching) corresponds to the assay carried out on the mice from batch 1. The third column (gray column) corresponds to the assay carried out on the mice from batch 2. The fourth column (black column) corresponds to the assay carried out on the mice from batch 5. The peptide composition according to the invention enables a reduction in the Enterobacteriaceae flora, induced by DSS, at a concentration of 0.1 g/kg/day. Enterobacteriaceae are associated with a pro-inflammatory potential;

the Firmicutes flora by quantitative amplification of the 16S ribosomal DNA on a fragment of the gene enabling analysis of diversity in the phylum. The ratio R of the amount of such a 16S ribosomal DNA to the amount of β-actin DNA is shown in FIG. 12. The first column (white column) corresponds to the assay carried out on control mice. The second column (column with diagonal hatching) corresponds to the assay carried out on the mice from batch 1. The third column (column with vertical hatching) corresponds to the assay carried out on the mice from batch 4. The fourth column (column with horizontal hatching) corresponds to the assay carried out on the mice from batch 3. The fifth column (gray column) corresponds to the assay carried out on the mice from batch 2. The sixth column (black column) corresponds to the assay carried out on the mice from batch 5. The peptide composition according to the invention induces a statistically significant reduction in the Firmicutes flora, induced by DSS, at concentrations of 0.1 g/kg/day ($p<0.05$), 1 g/kg/day ($p<0.05$) and 4 g/kg/day ($p<0.05$) but also induces a reduction in the non-induced Firmicutes flora at these same concentrations. It should be noted that an increase in the Firmicutes flora is generally observed in a known manner during digestive inflammation (IBDs, inflammatory bowel diseases);

the Bacteroidetes flora by quantitative amplification of the 16S ribosomal DNA on a fragment of the gene enabling analysis of diversity in the phylum. The ratio R of the amount of such a 16S ribosomal DNA to the amount of β-actin DNA is shown in FIG. 13. The first column (column with diagonal hatching) corresponds to the assay carried out on the mice from batch 1. The second column (column with vertical hatching) corresponds to the assay carried out on the mice from batch 4. The third column (column with horizontal hatching) corresponds to the assay carried out on the mice from batch 3. The fourth column (gray column) corresponds to the assay carried out on the mice from batch 2. The fifth column (black column) corresponds to the assay carried out on the mice from batch 5. The peptide composition according to the invention induces a statistically significant reduction in the Bacteroidetes flora, induced by DSS, at concentrations of 0.1 g/kg/day ($p<0.05$), 1 g/kg/day ($p<0.05$) and 4 g/kg/day ($p<0.05$). An increase in Bacteroidetes is generally observed in a known manner during digestive inflammation (IBD);

the *Faecalibacterium prausnitzii* flora by quantitative amplification of specific DNA. The ratio R of the amount of such a specific DNA to the amount of β-actin DNA is shown in FIG. 14. The first column (white column) corresponds to the assay carried out on control mice. The second column (column with diagonal hatching) corresponds to the assay carried out on the mice from batch 1. The third column (column with vertical hatching) corresponds to the assay carried out on the mice from batch 4. The fourth column (column with horizontal hatching) corresponds to the assay carried out on the mice from batch 3. The fifth column (gray column) corresponds to the assay carried out on the mice from batch 2. The sixth column (black column) corresponds to the assay carried out on the mice from batch 5. The peptide composition according to the invention induces a statistically significant increase in the *Faecalibacterium prausnitzii* flora, destroyed by DSS, at concentrations of 0.1 g/kg/day (p<0.01), 1 g/kg/day (p<0.01) and 4 g/kg/day (p<0.01). An increase in *Faecalibacterium prausnitzii* is generally observed in a known manner during digestive inflammation (IBD). *Faecalibacterium prausnitzii* also allegedly has anti-inflammatory properties;

the *Lactobacillus murinus* flora by quantitative amplification of specific DNA. The ratio R of the amount of such a specific DNA to the amount of β-actin DNA is shown in FIG. 15, in which the first column (white column) corresponds to the assay carried out on control mice. The second column (column with diagonal hatching) corresponds to the assay carried out on the mice from batch 1. The third column (column with vertical hatching) corresponds to the assay carried out on the mice from batch 4. The fourth column (column with horizontal hatching) corresponds to the assay carried out on the mice from batch 3. The fifth column (gray column) corresponds to the assay carried out on the mice from batch 2. The sixth column (black column) corresponds to the assay carried out on the mice from batch 5. The peptide composition according to the invention induces an increase in the *Lactobacillus murinus* flora at concentrations of 0.1 g/kg/day, 1 g/kg/day and 4 g/kg/day (p<0.05). *Lactobacillus murinus* also allegedly has anti-inflammatory properties.

Figure 19:
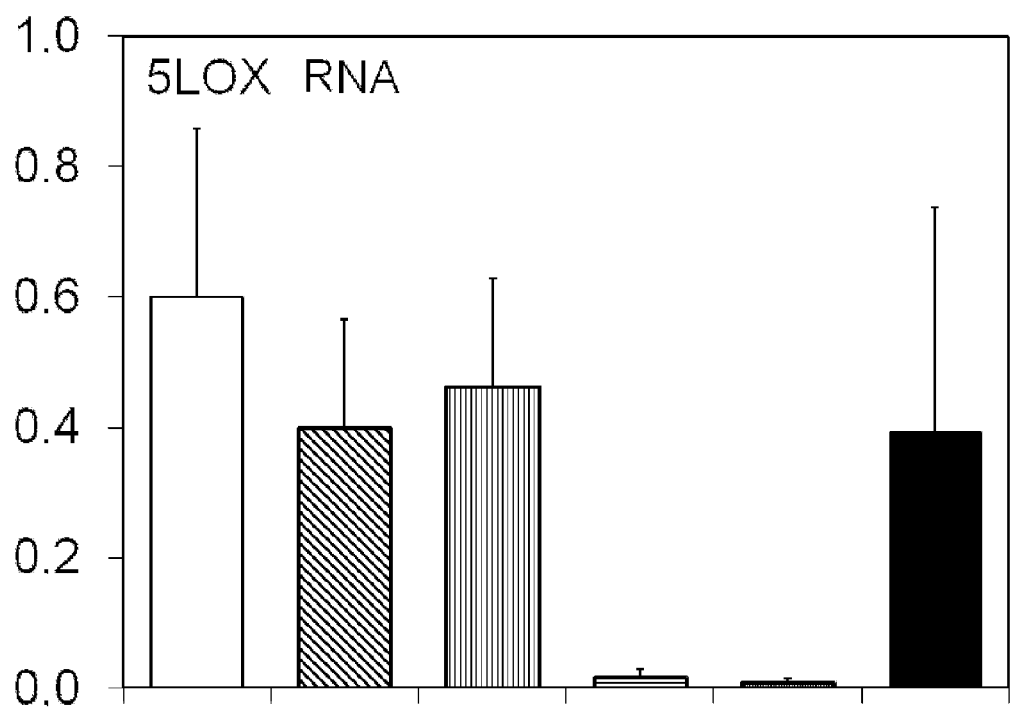
FIG. 19 is a graphical depiction in a histogram of an analysis by quantitative RT-PCR of the messenger RNA of 5-LOX in the colon of mice.
Figure 20:
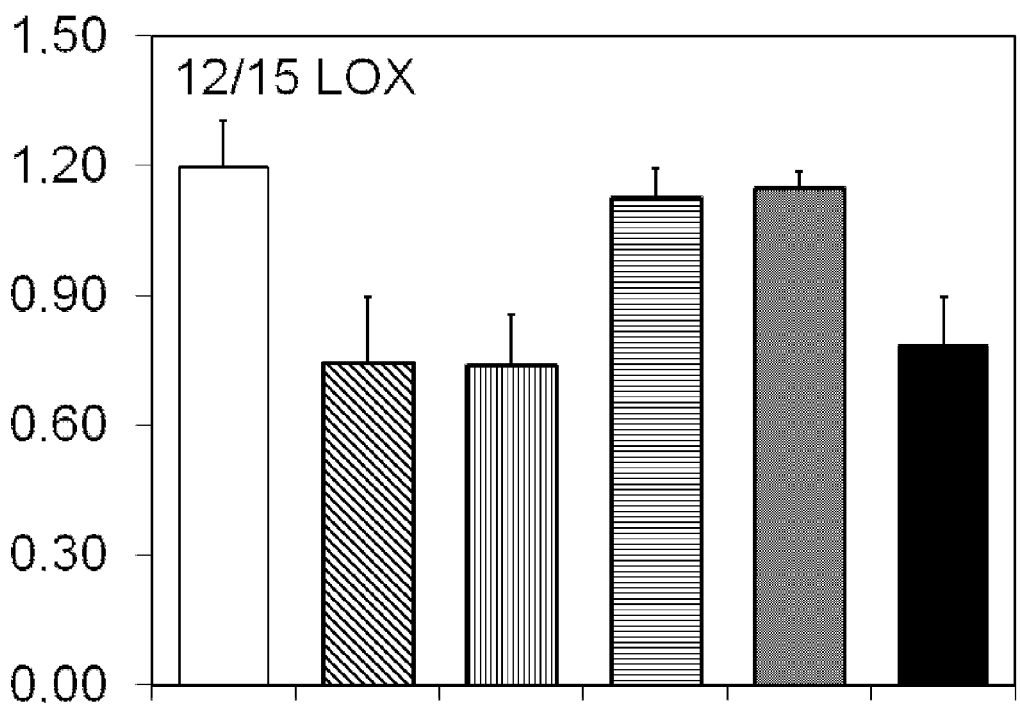
FIG. 20 is a graphical depiction in a histogram of an analysis by quantitative RT-PCR of the messenger RNA of 12/15-LOX in the colon of mice.

7. Effect of the Peptide Composition According to the Invention on Enzymes of the Lipid Metabolism of Arachidonic Acid:

5-LOX: The analysis by quantitative RT-PCR (reverse transcriptase polymerase chain reaction) of the messenger RNAs of the enzyme 5-lipoxygenase (5-LOX) is shown in FIG. 19, in which the first column (white column) corresponds to the analysis carried out on control mice. The second column (column with diagonal hatching) corresponds to the analysis carried out on the mice from batch 1. The third column (column with vertical hatching) corresponds to the analysis carried out on the mice from batch 4. The fourth column (column with horizontal hatching) corresponds to the analysis carried out on the mice from batch 3. The fifth column (gray column) corresponds to the analysis carried out on the mice from batch 2. The sixth column (black column) corresponds to the analysis carried out on the mice from batch 5. A statistically significant reduction in the expression of 5-LOX was observed for doses of the peptide composition according to the invention of 0.1 g/kg/day (p<0.01) and 1 g/kg/day (p<0.01) relative to the control not induced by DSS. The peptide composition according to the invention has an inhibitory effect on the expression of 5-LOX, promoting the production of pro-inflammatory lipid mediators;

12/15-LOX: The analysis by quantitative RT-PCR (reverse transcriptase polymerase chain reaction) of the messenger RNAs of the enzyme 12/15-lipoxygenase (12/15-LOX) is shown in FIG. 20, in which the first column (white column) corresponds to the analysis carried out on control mice. The second column (column with diagonal hatching) corresponds to the analysis carried out on the mice from batch 1. The third column (column with vertical hatching) corresponds to the analysis carried out on the mice from batch 4. The fourth column (column with horizontal hatching) corresponds to the analysis carried out on the mice from batch 3. The fifth column (gray column) corresponds to the analysis carried out on the mice from batch 2. The sixth column (black column) corresponds to the analysis carried out on the mice from batch 5. A statistically significant increase in the expression of 12/15-LOX was observed for doses of the peptide composition according to the invention of 0.1 g/kg/day (p<0.01) and 1 g/kg/day (p<0.01) relative to the control not induced by DSS.

It goes without saying that the invention may be subject to numerous variant embodiments and applications. In particular, different uses as medicament may vary without departing from the scope of protection of the invention.

The invention claimed is:

1. A peptide composition having an aminogram in which:
glycine is in a molar amount such that the ratio of this amount to the sum of the molar amounts of the amino acids in the composition is between 20.0% and 24.5%;
hydroxyproline is in a molar amount such that the ratio of this amount to the sum of the molar amounts of the amino acids in the composition is between 6.0% and 12.0%;
proline is in a molar amount such that the ratio of this amount to the sum of the molar amounts of the amino acids in the composition is between 10.6% and 14.6%;
the peptide composition having, during analysis by exclusion chromatography during which each peptide of the peptide composition is eluted with a retention time that is representative of the apparent molecular weight of this peptide, an elution curve of the peptides having an area under the curve value corresponding to the peptides of apparent molecular weight of less than 1400 Da such that the ratio of this area value to the total area under the curve is less than 40%;
said analysis being performed as described below:
on a filtration column of dimensions 300×7.8 mm comprising a stationary phase formed of a silica gel with a porosity of 5 μm;
the column being kept at a temperature of 40° C.;
with, as mobile phase, a solution formed (A) of ultrapure water comprising 0.1% by volume of trifluoroacetic acid and (B) of acetonitrile, wherein the A/B volume ratio is 75/25;
introducing, at the top of the gel filtration column, a volume of a solution comprising the peptide composition;
the flow rate of the mobile phase in the column being 0.6 ml/min, and;

the peptides of the composition being detected by absorbance at a wavelength of 214 nm.

2. The composition as claimed in claim 1, wherein each peptide of the composition has an apparent molecular weight of between 200 Da and 12000 Da.

3. The composition as claimed in claim 1, wherein the peptides have a mean apparent molecular weight of between 2500 Da and 3600 Da.

4. The composition as claimed in claim 1, wherein it has, by chromatographic analysis on an anion exchange column during which each peptide of the peptide composition is eluted from the column with a retention time that is representative of its charge:
- an area value under a peak corresponding to anionic peptides;
- an area value under a peak corresponding to neutral peptides, and;
- an area value under a peak corresponding to cationic peptides;
- such that the ratio of this area value under the peak corresponding to the anionic peptides to the sum of the area values under the peaks corresponding to the anionic peptides, to the neutral peptides and to the cationic peptides of the composition is between 27.0% and 45%;

the value of the area under the peak corresponding to the anionic peptides, the value of the area under the peak corresponding to the cationic peptides and the value of the area under the peak corresponding to the neutral peptides being determined by chromatographic analysis under the conditions described below:
- using a chromatographic column of dimensions 100× 7.8 mm comprising, as stationary phase, a hydrophilic anion exchange resin functionalized with quaternary ammonium groups with a particle size of 10 μm;
- using, as first mobile phase for elution of the cationic peptides and neutral peptides, a 5 mM aqueous Tris buffer (C) at pH 8.35 for a duration of 7 minutes starting from the introduction of the composition to be analyzed at the top of the column, then a second mobile phase for elution of the anionic peptides, in which the ratio of the volume of a buffer (D) formed of 5 mM Tris, 5 M NaCl at pH 8.35 to the volume of buffer (C) increases linearly from 0 to 100% in 30 minutes;
- with a flow rate of the mobile phase of 1 ml/min in the column;
- the analysis being performed at a temperature of 25° C., and;
- with detection by absorbance at a wavelength of 214 nm at the column outlet.

5. The composition as claimed in claim 1, wherein the peptides have, during a reversed-phase liquid chromatography hydrophobicity analysis, a retention time of between 16 min and 36 min;
said hydrophobicity analysis being performed under the conditions below:
- using a chromatography column of dimensions 250× 4.6 mm having a stationary phase formed of silica grafted with butyl groups, of a particle size of 5 μm and of a porosity value of 300 Å;
- using, as first mobile phase for elution of the hydrophilic peptides, a solution (E) of trifluoroacetic acid at 0.1% in ultrapure water for a duration of 7 minutes starting from the introduction of the composition to be analyzed at the top of the column, then a second mobile phase for elution of the hydrophobic peptides in which the ratio of the volume of a solution (F) of trifluoroacetic acid at 0.1% in water comprising 40% acetonitrile to the volume of the solution (E) increases linearly from 0 to 40% in 30 minutes;
- with a flow rate of the mobile phase of 0.6 ml/min in the column;
- the analysis being performed at a temperature of 40° C., and;
- with detection by absorbance at a wavelength of 214 nm at the column outlet.

6. The composition as claimed in claim 1, wherein the composition is in a liquid state.

7. The composition as claimed in claim 1, wherein the composition is in a solid state.

8. The composition as claimed in claim 1, wherein the composition is devoid of carbohydrate.

9. The composition as claimed in claim 1, wherein the composition is devoid of fats.

10. The composition as claimed in claim 1, wherein the peptides of the composition are water-soluble.

11. The composition as claimed in claim 1, wherein the peptides of the composition result from a controlled enzymatic hydrolysis of collagen from skin of at least one fish selected from the group formed of fish from the family Pangasiidae and from the family Cichlidae.

12. The composition as claimed in claim 1, wherein the peptide composition is extracted from a skin of a fish previously pretreated with an acid treatment.

13. A medicament comprising the composition as claimed in claim 1.

14. A human food composition comprising the composition as claimed in claim 1.

* * * * *